(12) United States Patent
Al-Ali et al.

(10) Patent No.: US 8,353,842 B2
(45) Date of Patent: Jan. 15, 2013

(54) PORTABLE PATIENT MONITOR

(75) Inventors: Ammar Al-Ali, Tustin, CA (US); Chris Schulz, Rocklin, CA (US); Massi E. Kiani, Laguna Niguel, CA (US); Roger C. Wu, Irvine, CA (US); Garrick Maurer, Newport Beach, CA (US)

(73) Assignee: Masimo Corporation, Irvine, CA (US)

( * ) Notice: Subject to any disclaimer, the term of this patent is extended or adjusted under 35 U.S.C. 154(b) by 828 days.

(21) Appl. No.: 12/343,345

(22) Filed: Dec. 23, 2008
(Under 37 CFR 1.47)

(65) Prior Publication Data

US 2009/0306488 A1    Dec. 10, 2009

Related U.S. Application Data

(63) Continuation of application No. 11/061,090, filed on Feb. 18, 2005, now abandoned.

(51) Int. Cl.
*A61B 5/02* (2006.01)
*A61B 6/00* (2006.01)

(52) U.S. Cl. ......... 600/502; 600/500; 600/476; 600/479

(58) Field of Classification Search .......... 600/473–481, 600/483, 500–504
See application file for complete search history.

(56) References Cited

U.S. PATENT DOCUMENTS

| | | | |
|---|---|---|---|
| 4,030,483 A * | 6/1977 | Stevens | 600/479 |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| 5,443,065 A * | 8/1995 | Berghoff et al. | 600/384 |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,482,036 A | 1/1996 | Diab et al. | |
| 5,490,505 A | 2/1996 | Diab et al. | |

(Continued)

OTHER PUBLICATIONS

Smith Medical PM, Inc., "FingerPrint® Sleep Hand-Held Puse Oximeter", Catalog No. 3403-000, 2004.

(Continued)

*Primary Examiner* — Navin Natnithithadha
(74) *Attorney, Agent, or Firm* — Knobbe, Martens, Olson & Bear LLP

(57) ABSTRACT

Embodiments of the present disclosure includes a portable pulse oximeter, such as a handheld pulse oximeter, that provides a user with intuitive key navigation for device operation, which reduces an amount of visual concentration needed to handle and operate the oximeter. In various embodiments, the portable pulse oximeter includes one or more of user input keys disposed along curve, an alignment edge providing guidance by feel of a user's digits to the input keys, raised convex keys also providing navigation by feel, a protective boot disposed around various portions of the oximeter housing to protect against impacts, a table-top stand, combinations of the same, or the like.

20 Claims, 24 Drawing Sheets

U.S. PATENT DOCUMENTS

| | | |
|---|---|---|
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,722,412 A | 3/1998 | Pflugrath et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,508,451 B1 | 1/2003 | Blythe et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,731,962 B1 | 5/2004 | Katarow et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,780,154 B2 | 8/2004 | Hunt et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,899,273 B2 | 5/2005 | Hussey et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |

| Patent | Date | Inventor |
|---|---|---|
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,689,269 B2 * | 3/2010 | Thurston et al. ............... 600/477 |
| 7,738,946 B2 * | 6/2010 | Thurston et al. ............... 600/477 |
| 2002/0140675 A1 | 10/2002 | Al et al. |
| 2003/0013975 A1 | 1/2003 | Kiani |
| 2006/0062626 A1 | 3/2006 | Hamilton et al. |

OTHER PUBLICATIONS

Smiths Medical, "Pulse Oximeter for Sleep Screening, Operation Manual", Catalog No. 1884SS, Version 1, Apr. 2002.

MiniCorr Digital Hand Held Pulse Oximeter, Jan. 30, 2004, http://www.spservices.co.uk/product_info.php/manufacturers_id/17/products_id/1914.

BCI FingerPrint Pulse Oximeter Inc Printer, Jan. 30, 2004, http://www.spservices.co.uk/product_info.php/manufacturers_id/17/products_id/1915.

BCI 3003 Rechargeable Sat-Pac Pulse Oximeter, Jan. 30, 2004, http://www.spservices.co.uk/product_info.php/manufacturers_id/17/products_id/1918.

* cited by examiner

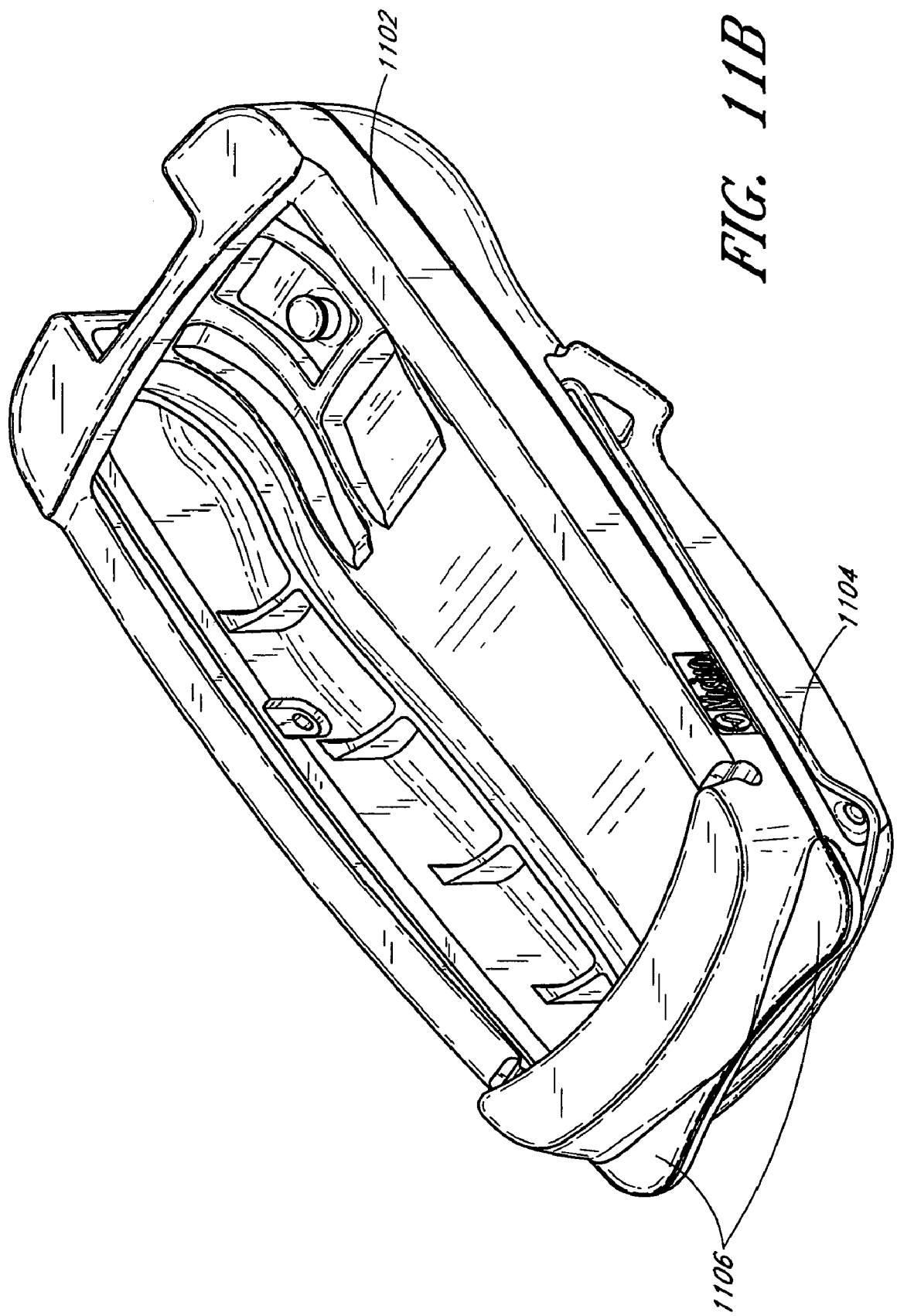

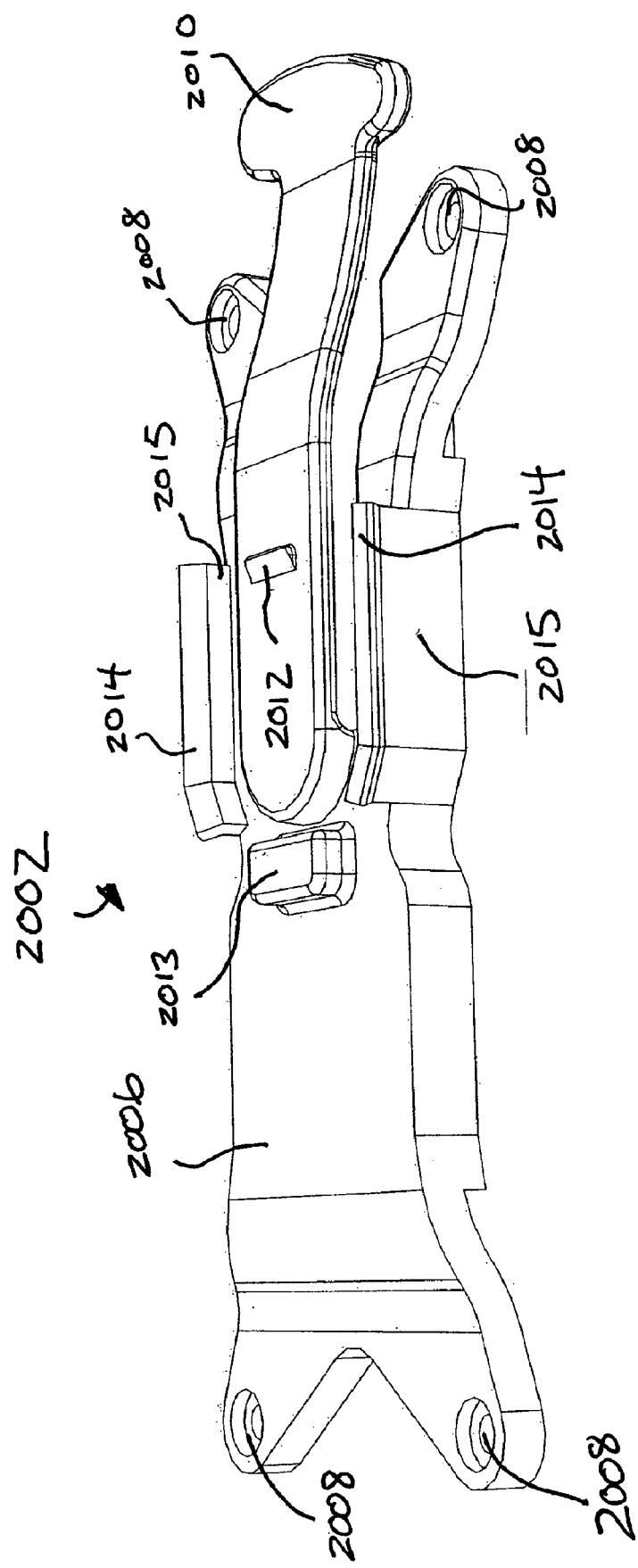

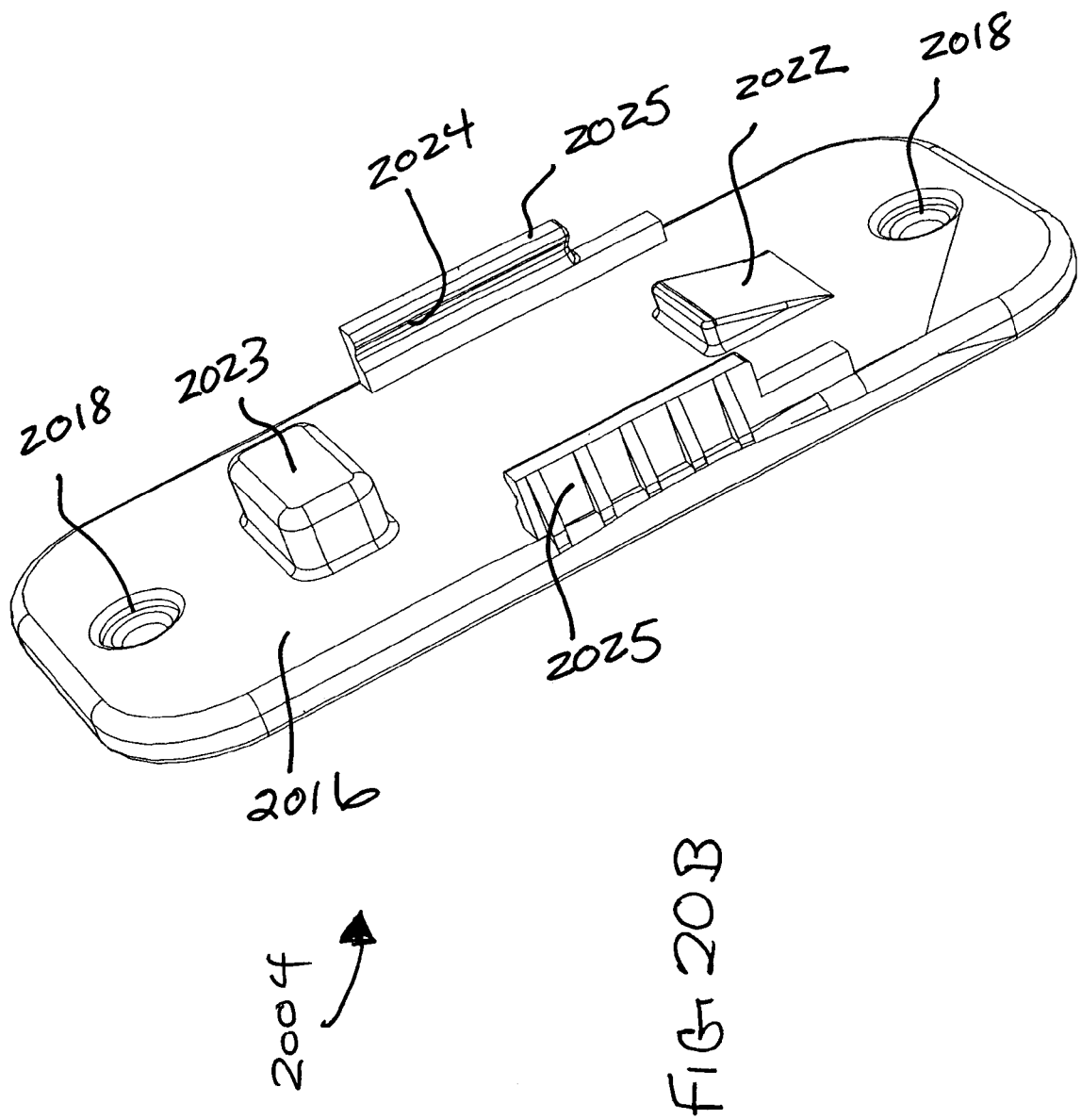

PORTABLE PATIENT MONITOR

REFERENCE TO RELATED APPLICATION

The present application claims priority benefit under 35 U.S.C. §120 to, and is a continuation of U.S. patent application Ser. No. 11/061,090, filed Feb. 18, 2005 entitled "Portable Patient Monitor." The present application also incorporates the foregoing disclosures herein by reference.

BACKGROUND OF THE DISCLOSURE

1. Field of the Disclosure

The present disclosure relates to the field of patient monitoring devices. More specifically, the disclosure relates to portable and handheld patient monitors, including pulse oximeter monitors, while other embodiments relate to various parameters displayed by these type of patient monitors.

2. Description of the Related Art

Caregivers often employ patient monitoring systems or devices, such as pulse oximeters, capnographs, blood pressure cuffs, and the like, for convenient spot checking and even continuous monitoring of physiological characteristics of a patient. Patent monitoring systems generally include one or more sensors applied to a patient, a monitoring device, and one or more cables connecting the one or more sensors and the monitoring device.

Portability of these monitoring systems is advantageous for a number of reasons. For example, portable devices provide the patient with mobility and provide the caregiver the option of including the monitoring device when transporting patients from one setting to another. For example, caregivers often transport patients from an ambulance to a hospital emergency room, and between surgical, intensive care, and recovery settings.

Some portable devices can also alleviate issues relating to incompatibility problems exacerbated by the prevalence of expensive and non-portable multiparameter patient monitoring systems. For example, some portable patient monitoring devices are capable of outputting information expected by one or more non-portable legacy multiparameter patient monitoring systems, where that output is used as an input for the non-portable systems.

One example of a patient monitoring device is a pulse oximeter, which is a widely accepted noninvasive procedure for measuring the oxygen saturation level of arterial blood, an indicator of oxygen supply. Early detection of low blood oxygen level is critical in the medical field, for example in critical care and surgical applications, because an insufficient supply of oxygen can result in brain damage and death in a matter of minutes. However, many other industries have adopted the detection of a person's oxygen supply into their monitoring and analysis regimens, including the fitness industry, home or corporate care industries, elderly care facilities and the like.

A pulse oximeter typically provides a numerical readout of the patient's oxygen saturation, a numerical readout of pulse rate, and an audible indicator or "beep" that occurs in response to each pulse. In addition, the pulse oximeter may display the patient's photo plethysmograph, which provides a visual display of the patient's pulse contour and pulse rate.

A portable pulse oximeter may be a standalone device, or as described in the foregoing, may be incorporated as a module or built-in portion of a multiparameter patient monitoring system, which also provides measurements such as blood pressure, respiratory rate, EKG, or the like. Exemplary pulse oximeters, including standalone pulse oximeters and portable pulse oximeters usable within a multiparameter system, are commercially available from Masimo Corporation of Irvine California, the Assignee of the present application. Aspects of such exemplary pulse oximeters are disclosed in U.S. Pat. Nos. 6,770,028, 6,584,336, 6,263,222, 6,157,850, 5,769,785, and their related patent and copending application families, each of which is incorporated herein by reference.

In many conventional patient monitoring devices, such as pulse oximeters, the interaction between a caregiver and the device is accomplished through user input keys and displayed data. The user input keys are arranged in a topology or layout similar to a table where the input keys are aligned in one or more rows and/or one or more columns. In portable devices, such layouts do not provide an intuitive feel, often requiring a user to use both hands to operate the device. For example, caregivers often use one hand to hold the device and the other to punch the input keys. Such layouts also often engage the full attention and concentration of the caregiver for operation. Moreover, such row and/or column key layouts can even lead to losing one's grip on the device when attempting single-handed operation or when inattentively operated. Loss of grip can lead to the device being dropped, knocked out of hand, off a counter, or the like, which can damage the device and/or lead to inaccurate patient monitoring.

SUMMARY OF THE DISCLOSURE

Embodiments of the present disclosure seek to overcome some or all of the foregoing and other problems. For example, embodiments of the present disclosure include a portable patient monitor, such as a handheld pulse oximeter, that provides a user with intuitive key navigation and device operation, which reduces an amount of visual concentration needed to handle and operate the patient monitor. In various embodiments, the portable patient monitor includes one or more of user input keys disposed along curve, an alignment edge, raised convex keys providing navigation-by-feel, a bezel or protective boot disposed around various portions of the housing to resist impacts, a rubber cable connector housing, a table-top stand, combinations of the same, or the like. Such intuitive navigation-by-feel provides for optional single handed operation and reduced visual concentration on the input keys, which advantageously allows caregivers to give at least some of their attention to, for example, the display of current and/or past monitored data, the patients themselves, other caregivers, or the like.

In addition to the forgoing, embodiments of the present disclosure also provide intuitive output of data relating to monitored physiological parameters. For example, an embodiment of the monitoring device includes display indicia corresponding to an indication of the perfusion through a measurement site. In an embodiment, the indicia includes an LED bar display, or Pulse Amplitude Index (PAI) or (PI), which may be used as a diagnostic tool during low perfusion for the accurate prediction of illness severity, especially in neonates.

In an embodiment, the PAI bar can grow in height, can change color, can combine with one or more audible or visual alarms including audio or visual alarms that change pitch, on-off frequency, color, intensity, combinations of the same, or the like. In a preferred embodiment, the PAI LED bar is highest and green when the perfusion at the site is best, and lowest and red when the perfusion is worst.

An artisan will also recognize from the disclosure herein that other indicators can be used to indicate the same or other data. For example, digital and/or pictorial displays can display values for the foregoing or other monitored data and the displays may combine with audio or other visual indicators, such as pitch or beat. Moreover, an artisan will recognize from the disclosure herein that the LED bars can be used to show additional data, such as, for example, a signal quality. In an embodiment of such signal quality indicators, the signal quality (SQ) LED bar can grow in height as the quality of the signal increases, can change color as the quality increases, combinations of the same, or the like. In a preferred embodiment, the SQ LED bar is highest and green when the quality of the site is best, and lowest and red when the quality is worst. In an embodiment, a signal quality indicator may comprise a single LED, preferably lighting red when the quality is worse and optionally lighting green when the quality is better. This type of signal quality LED may combine flashing, changing the frequency of the flashing, audible alarms, and the like to ensure caregiver notices the measurement of signal quality.

Moreover, in an embodiment, the patient monitor may include an indicator designed to inform a caregiver on whether a particular medical sensor is properly attached to the body tissue at the measurement site on the patient. For example, an advanced probe off detection (APOD) indicator may comprise a single LED, preferably lighting red when one or more connected medical sensors is not properly attached, optionally lighting green when the attachment is better. This type of probe off detection may combine flashing, changing the frequency of the flashing, audible alarms, and the like to ensure caregiver notices whether the monitor is receiving data indicating improper attachment of a medical probe. Examples of the signal processing involved with the determination of probe off detection are disclosed in U.S. Pat. Nos. 6,526,300, 6,771,994, 6,360,114, 6,654,624, and their related patent and copending application families, each of which is incorporated herein by reference.

Accordingly, an embodiment of the present disclosure includes a patient monitoring device comprising electronic circuitry capable of receiving a signal output from a light sensitive detector capable of detecting light attenuated by body tissue carrying pulsing blood. The electronic circuitry is also capable of outputting audio or visual indicia indicative of one or more physiological parameters of the body tissue. The device further includes a housing including a top side, and a plurality of user input keys arranged on the top side of the housing along the periphery of one or more curves.

Another embodiment includes a patient monitoring device comprising electronics capable of receiving a sensor output and outputting audio or visual data indicative of one or more physiological parameters. The device also includes an outer body housing the electronics and including a top surface having periphery edges defining an approximate shape of the outer body. The device further includes a plurality of keys disposed on the top surface of the outer body, and at least one alignment edge shaped to allow a user to determine by feel a location of the plurality of keys by sliding one or more digits along the at least one alignment edge.

For purposes of summarizing the disclosure, certain aspects, advantages and novel features of the disclosure have been described herein. Of course, it is to be understood that not necessarily all such aspects, advantages or features will be embodied in any particular embodiment.

BRIEF DESCRIPTION OF THE DRAWINGS

A general architecture that implements the various features of the disclosure will now be described with reference to the drawings. The drawings and the associated descriptions are provided to illustrate embodiments of the disclosure and not to limit the scope of the disclosure. Throughout the drawings, reference numbers are re-used to indicate correspondence between referenced elements. In addition, the first digit of each reference number indicates the figure in which the element first appears.

FIGS. 11B-11C illustrate top and bottom perspective views of the protective boot cover and stand of FIG. 11A.

FIGS. 20A-20D illustrate perspective views of an exemplary mechanical latching mechanism for attaching a portable patient monitor to another surface, such as a device, a wall, a bed, or the like.

DETAILED DESCRIPTION OF THE PREFERRED EMBODIMENT

Figure 1:
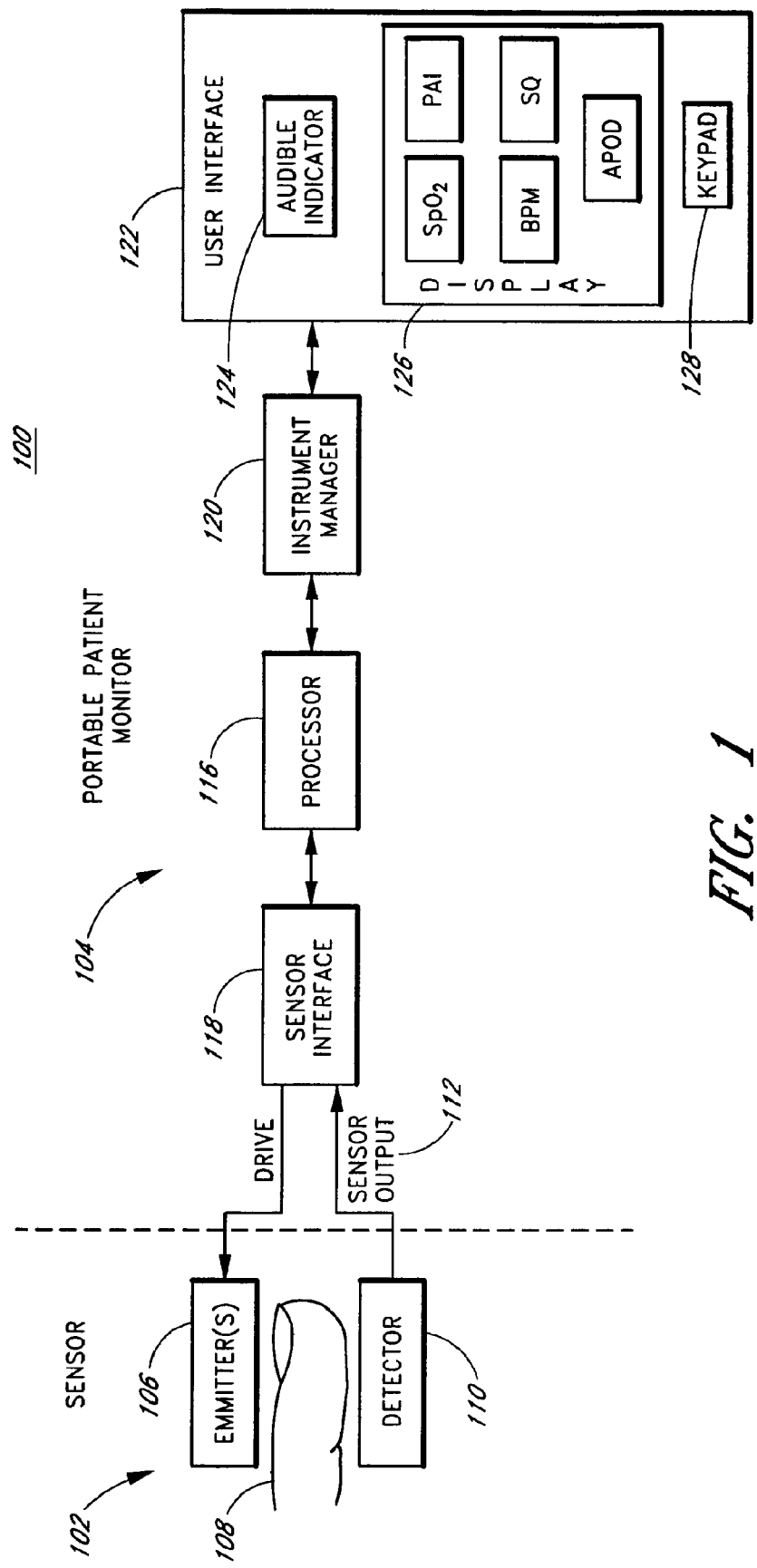
FIG. 1 illustrates a block diagram of a patient monitoring system including a sensor and a portable patient monitor according to embodiments of the present disclosure.

Embodiments of the present disclosure include a patient monitor, such as a handheld portable patient monitors, that provides a user with intuitive key navigation. For example, the portable patient monitor includes a unique layout of user input keys and one or more elements providing a user the ability to navigate the layout by feeling those elements. Such intuitive operation advantageously reduces an amount of visual concentration needed to handle and operate the patient monitor.

In various embodiments, a portable patient monitor includes one or more of user input keys disposed along one or more curves. The one or more curves may roughly correspond to a sweeping motion of a user's thumb across the top side of the housing on a hand in which the user holds the portable patient monitoring device. Although preferably irregular shaped, the one or more curves may also or alternatively roughly correspond to a segment of a circle's circumference, where a radius of the circle roughly corresponds to an operator's thumb. Additionally or alternatively, the one or more curves may advantageously be substantially parallel to one or more alignment edges. For example, the monitoring device can include one or more protruding or groove-like edges which intuitively lead the operator's fingers to the various keys in the keypad layout. In an embodiment, the alignment edge is raised and at least partially surrounds the layout. In one embodiment, the alignment edge forms an approximate irregular "V" shape, where a first side of the "V" is substantially parallel to a side of the patient monitor housing. The first side also includes an edge tapered down from a high point at the vertex of the "V." The other side of the irregular "V" is curved roughly mirroring the sweep of an operator's thumb. While preferred, an artisan will recognize from the disclosure herein that tapering from the vertex of the "V" is optional and a wide variety of other edge formations that guide the operator through the keypad layout are possible, including, for example, multiple substantially parallel edges, indentations, perforated edges, irregular shapes such as the dimples of a golf ball, combinations of the same or the like.

The foregoing alignment edge advantageously provides navigation-by-feel of the input keys by a user's digits, such as the user's thumb. Additionally, the actual keys can provide increased navigation-by feel. In an embodiment, the keys include raised convex keys that feel like bumps on the surface of the housing. Such bumps may also comprise unique shapes or surface textures to further identify the respective input key and/or its function to the operator.

In addition to the foregoing input key layout and alignment edges, an embodiment of the present disclosure includes a portable patient monitor that includes a pliable raised bezel or edge, such as rubber, to absorb some or all of an impact due to a loss of grip, an inadvertent fall from a table or bed, or the like. Additionally, the foregoing alignment edge may also be formed from a material that protects the display surface from accidental impacts. In an embodiment, a protective impact resistant boot may be disposed around various portions of the monitor. Moreover, in an embodiment, the electronic displays or display panel can advantageously be recessed slightly with respect to the monitor housing such that the likelihood of contact between the electronic displays and any potential damaging impacts is greatly reduced. In an embodiment, the foregoing alignment edge assists in raising the housing above the plane of the electronic displays.

Other useful ergonomic features disclosed herein include a cable connector housing made of pliable materials, such as rubber, to protect against damaging impacts, create a secure connection to a sensor cable, protect a wearer of the sensor from sharp edges, and the like. Moreover, a table-top stand may provide a staging element to conveniently position the monitor on a table, affix the monitor to a bed rail, or the like. In an embodiment, the table top stand includes a protectable boot and a retractable stand. When the stand is retracted, the boot can be left connected to the housing of the monitor to protect the monitor from damaging impacts. In an embodiment, the boot is comprises of a pliable material such as rubber.

To facilitate a complete understanding of the disclosure, the remainder of the detailed description describes the disclosure with reference to the drawings, wherein like reference numerals are referenced with like numerals throughout.

FIG. 1 illustrates a block diagram of a portable patient monitoring system 100 including a sensor 102 and a portable patient monitor 104 according to embodiments of the present disclosure. The monitor 104 receives an output signal from the sensor 102 indicative of an amount of absorption of light by body tissue at a measurement site. The term "body tissue" includes its broad ordinary and customary meaning, including body constituents, tissues, fluids including blood, and the like. The sensor 102 can include one or more emitters 106 capable of emitting light into body tissue 108 such as a finger, toe, ear, forehead, or the like. One or more light sensitive detectors 110 detect the light after it has been attenuated by the body tissue 108 and outputs a signal indicative thereof on cable 112. Some sensors 102 include the cable 112, such as some reusable sensors, while other sensors 102 connect to the cable 112 through sensor and cable connectors, such as those disclosed in Des. Pat. No. 393,830 and U.S. Pat. No. 5,645,440, and their related patent families, each of which are incorporated by reference herein.

FIG. 1 also shows the monitor 104 including one or more microprocessors 116, a sensor interface 118, an instrument manager 120, and a user interface 122, including an audible indicator 124, a display 126, and a user keypad 128 comprising one or more user input keys. In an embodiment, the display 126 may include one or more displayed parameters, including parameters relating to oxygen saturation, $SpO_2$, pulse rate, BPM, a perfusion amplitude index, PAI or PI, SQ or SIQ, probe off detection, APOD, or the like.

In an embodiment, the processor 116 comprises a one or more integrated or other electronic circuits capable of executing software or hardware instructions in order to determine representative values for one or more monitored patient parameters. The sensor interface 118 provides an LED drive current which, for example, may alternately activate the emitters 106. The sensor interface 118 also may comprise input circuitry for amplification and filtering of a sensor output signal generated by the detector 110, which includes information relating to light energy attenuated from transmission through the patient tissue 108. In an embodiment, the sensor interface 118 may advantageously comprise a multifunction communications port capable of communicating the foregoing signals to and from an attached sensor 102, or when determined appropriate, the sensor interface 118 may advantageously be capable of communication with one or more connected computing devices. The communication may be serial or parallel depending upon for example, an amount of available conductors. Such multifunction ports advantageously reduce the number of input/output circuitry by providing multiple functions through the same electrical connection depending upon, for example, a connected sensor or a connected instrument.

The instrument manager 120 provides hardware and software interfaces for managing the user interface 122, including the audible indicator 124, the display 126, and the keypad 128.

In an embodiment, the audible indicator 124 can comprises one or more transducers to generate human perceptible sound indicating, for example, pulse beeps as well as various alarms. The display 126 comprises one or more visual indicators of the one or more monitored parameters. For example, the display 126 may comprise LEDs, 7-segment displays, LCDs, bar graph displays, icons, traces such as plethysmograph or other traces, or the like. According to one embodiment, the display 126 includes at least visual indications of $SpO_2$ and PAI, as will be discussed in greater detail herein.

Although the patient monitoring system 100 is disclosed with reference to the foregoing embodiment, the disclosure is not intended to be limited thereby. Rather, a skilled artisan will recognize from the disclosure herein a wide number of alternatives for the patient monitoring system 100.

Figure 2A:
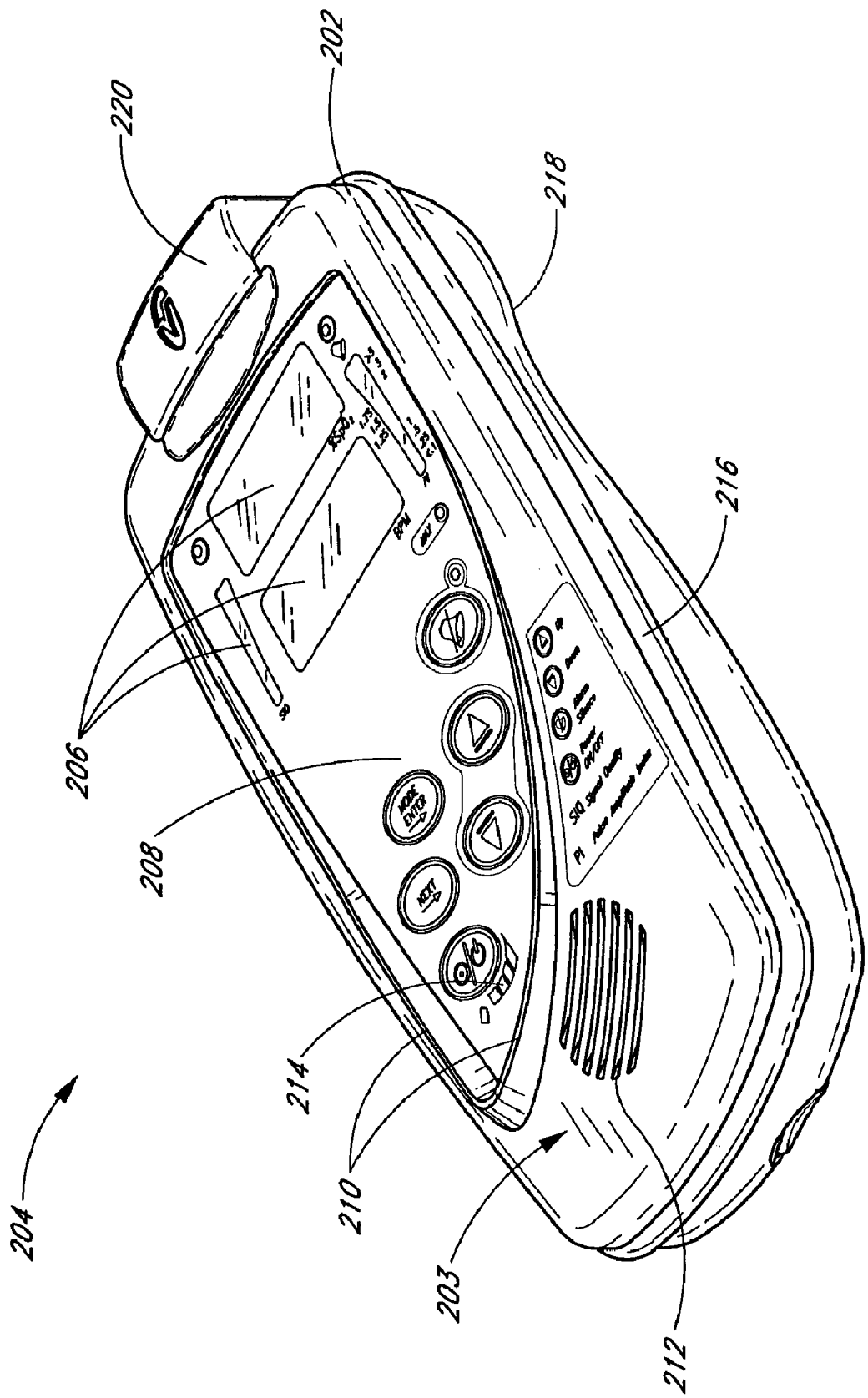
FIGS. 2A-2B illustrate front top and front bottom perspective views of an embodiment of the portable patient monitor of FIG. 1.

FIG. 2A illustrates a front top perspective view of an embodiment of a portable patient monitor 204. According to one embodiment, the monitor 204 comprises electronic circuitry including some or all of the electronics and displays capable of performing some or all of the functionality disclosed with reference to the monitor 104.

As shown in FIG. 2A, the monitor 204 includes a housing 202 including a top side 203 comprising a parameter display portion 206, a keypad 208, an alignment edge 210, a speaker grating 212, a battery power indicator 214, a protective bezel 216, one or more grip enhancement portions 218, and a cable connector 220.

In an embodiment, the housing 202 comprises plastic or plastic-like materials, optionally manufactured as a two piece injection mold. However, a skilled artisan will recognize a wide variety of suitable materials and manufacturing techniques for the housing 202.

FIG. 2A also shows the alignment edge 210 as an edge raised above the top side 203 of the housing 202, shaped as an approximate irregular "V" shape as discussed above. In the illustrated embodiment, the operator of the monitor 204 can feel the alignment edge, which intuitively leads the operator's fingers/thumb to the various keys in the keypad 208, advantageously providing navigation-by-feel functionality to the housing 202. In an embodiment, the alignment edge 210 includes a first side substantially parallel to a side of the patient monitor housing, where the first side includes a raised edge tapered down from a high point near the vertex of the "V." The other side of the irregular "V" is curved roughly mirroring the sweep of an operator's thumb over the keypad 208. While preferred, an artisan will recognize from the disclosure herein that the alignment edge 210 can comprise multiple substantially parallel edges, indentations, perforated edges, irregular shapes such as the dimples of a golf ball, combinations of the same or the like.

In an embodiment, the input keys of the keypad 208 also provide navigation-by-feel functionality. For example, the keys may comprise convex buttons raised above the display panel, where the convex buttons rise sufficiently that a user's thumb can easily distinguish between the display panel and the convex buttons. Moreover, in an embodiment, each raised convex button may include indicia, such as indentations, perforated edges, irregular shapes such as the dimples of a golf ball, combinations of the same or the like, that assist in identifying each key or convex button to a caregiver without the caregiver needing to look at the particular key.

FIG. 2A also shows the protective bezel 216 substantially surrounding the side periphery of the housing 202. According to an embodiment, the bezel comprises a pliable material, such as, for example, rubber, capable of absorbing at least some of a wide variety of impacts that the portable monitor 204 might incur. According to another embodiment, other portions of the housing 202 comprise pliable materials in order to better protect the monitor 204 from damaging impacts. For example, the alignment edge 210, the cable connector 220, and the like may comprise impact absorbing materials.

FIG. 2A also shows the cable connector 220. As discussed in the foregoing, the cable connector 220 comprises the electronic connection elements for appropriately connecting to a cable communicating signals to and from a physiological sensor, such as, for example, the sensor 102. In an embodiment, the cable connector 220 may advantageously comprise the above-described multifunction port.

Figure 2B:
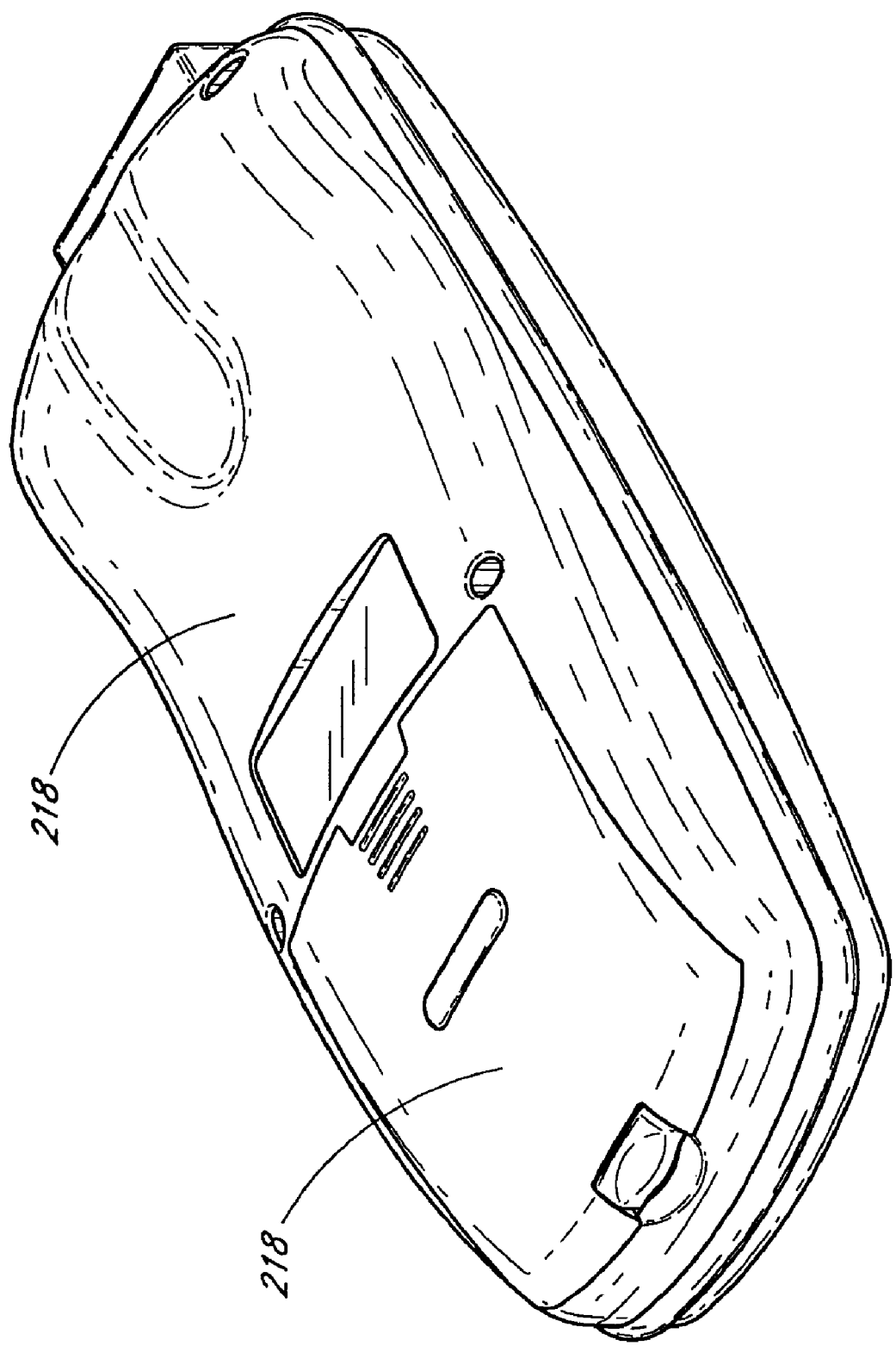
Figure 4A:
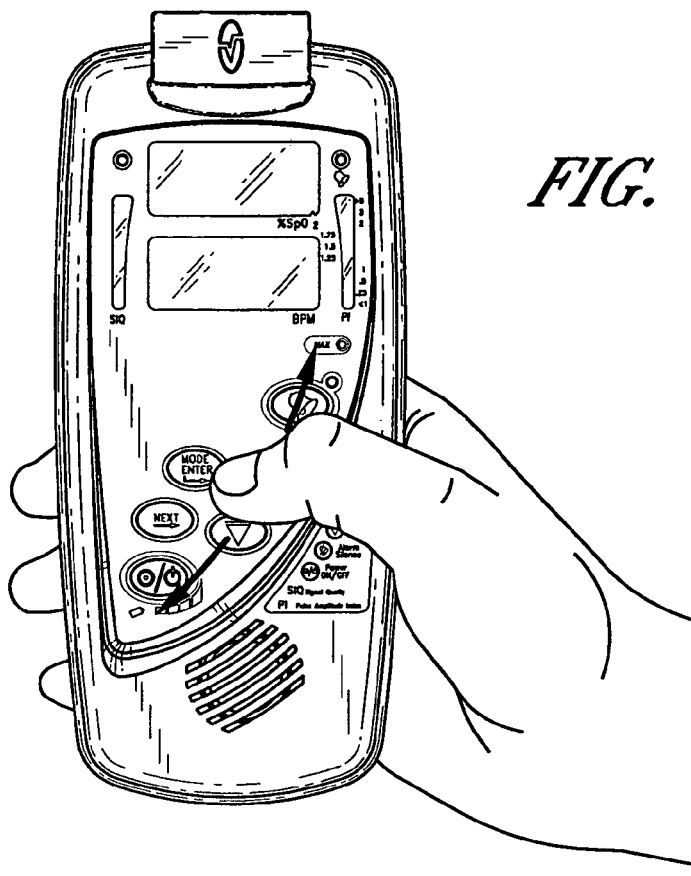
FIGS. 4A-4B illustrate right and left hand operation of an embodiment of the portable patient monitor of FIG. 2.
Figure 4B:
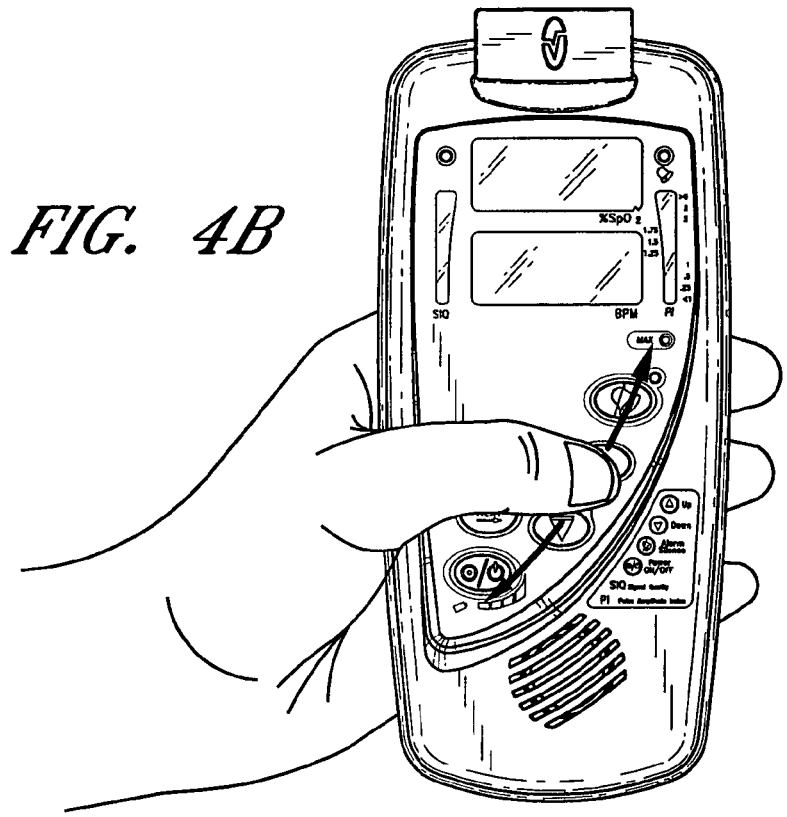

FIG. 2B illustrates a front bottom perspective view of an embodiment of the monitor 204. As shown in FIG. 2B, the housing 202 of the monitor 240 also includes the one or more grip enhancement portions 218 comprising, for example, an indented or concave portion shaped to comfortably and ergonomically fit the fingers of an operator, and a protruded or convex portion shaped to comfortably and ergonomically fit within a palm of a hand of the operator. Therefore, when the operator holds the monitor 204 as shown in FIGS. 4A-4B, the monitor 204 fits securely and comfortably in the operator's grip.

Figure 3:
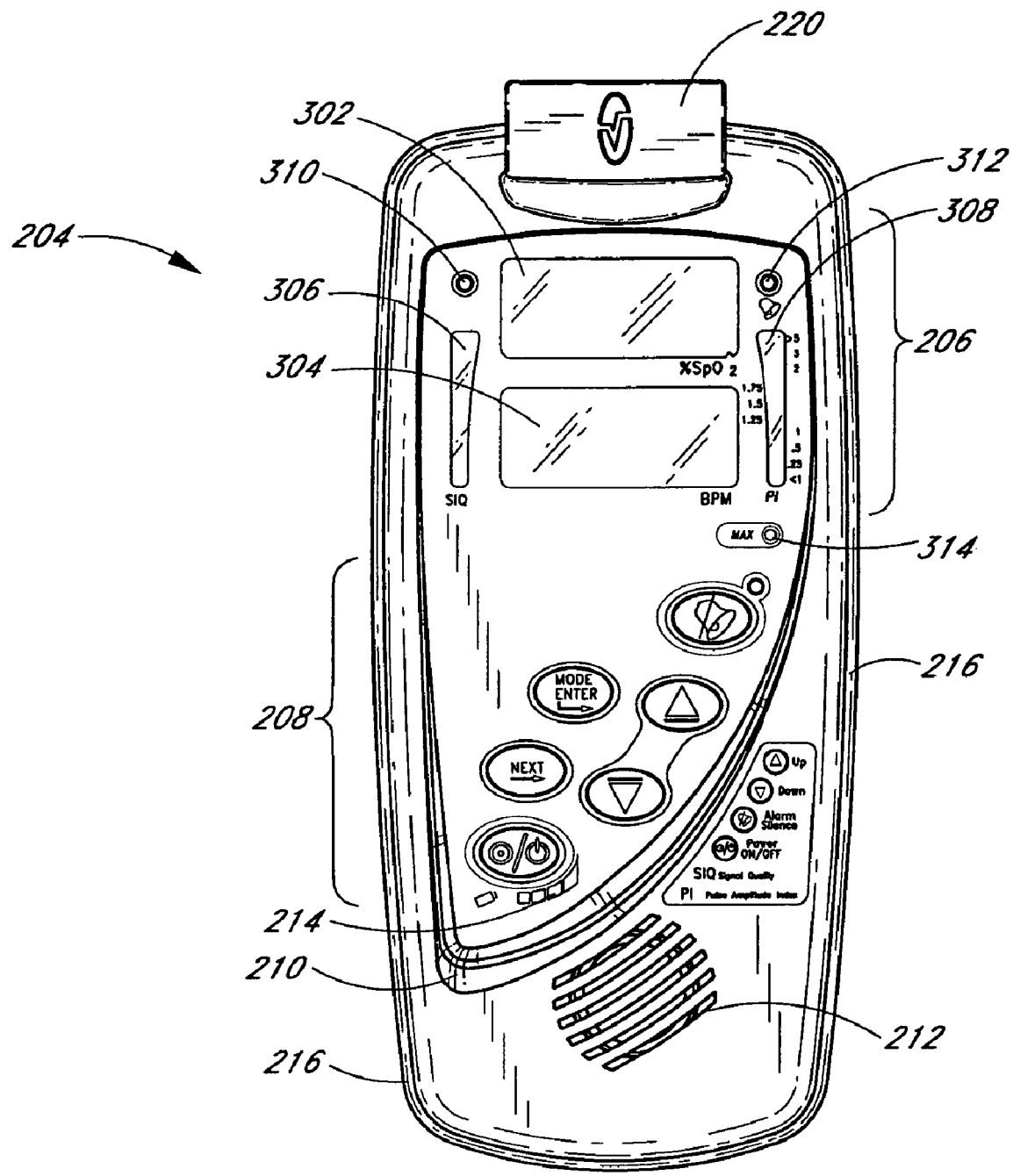
FIG. 3 illustrates a top plan view of an embodiment of the portable patient monitor of FIG. 2.

FIG. 3 illustrates a top plan view of an embodiment of the portable patient monitor 204. As shown in FIG. 3, the monitor 204 includes the parameter display portion 206, where the monitor 204 presents visual indications of one or more monitored physiological parameters. As shown, the display portion 206 comprises two 7-segment displays, 302 and 304, two LED bar graphs, 306 and 308, a plurality of alarms, 310 and 312, and an indication of the quality of the input signal(s) 314. In an embodiment, the 7-segment display 302 displays a measurement oxygen saturation, SpO2, as a percentage between about 0 and about 100%, while the 7-segment display 304 displays an indication of pulse rate between about 25 and 240 beats-per-minute.

Additionally, the display portion 206 includes the plurality of LED bar graph or gas meter style displays, 306 and 308, and single LED alarms, 310, 312, and 314. In one embodiment, the bar graph 308 provides a perfusion amplitude index, PAI, as will be discussed in greater detail with reference to FIG. 19. The PAI bar graph display 308 indicates a measurement of perfusion percentage between about 0.02% and about 20%. However, an artisan will recognize from the disclosure herein that a wide variety of other ranges with other granularities could be used. The bar graph 306 provides a signal quality LED bar graph display may indicate a measurement of signal quality where the amplitude of the bar graph represents an increasing measure of signal quality. However, an artisan will also recognize from the disclosure herein a wide variety of data, ranges, and granularities can be employed to illustrate signal quality.

In an embodiment, the bar of the bar graph 308 grows in height as, for example, the value of the parameter displayed becomes more physiologically normal or desirable, while the bar graph 306 grows in height as, for example, the value of the parameter displayed becomes more physiologically dangerous. Additionally or alternatively, the color of the parameter can change from red to yellow to green as, for example, the value of the parameter displayed becomes more physiologically normal or desirable. Moreover, the displays may pulse or flash with greater or lesser frequency as the value becomes more or less desirable, may pulse with the heartbeat, or may be combined with an audible indicator capable of varying the audible signal in pitch, volume, and/or beep frequency in similar manners to those described with respect to the displays.

An artisan will recognize from the disclosure herein that one or both bar graph displays could be changed to represent other data, such as, for example, a measurement of signal quality, an indication of proper application of the sensor to a test site (probe off detection), various alarms, a fast indication of $SpO_2$ designed to track rapid changes therein, or the like.

In an embodiment, the single LED alarms 310, 312, and 314 comprise a red and optionally flashing LED when the calculated levels of PAI, signal quality, or the like are below, or where appropriate, above predetermined thresholds, and are solid green, clear, or off when those values are physiologically normal or desirable. In yet another embodiment, the monitor 204 use the audible indicator 124 in conjunction with the foregoing visual alarms to alert caregivers to parameter values below, or where appropriate, above certain predetermined threshold values or patterns.

FIG. 3 also shows the keypad 208 comprising a plurality of user keys used to input commands or instructions to the monitor 204. As shown in FIG. 3, the keypad layout 208 provides a user with intuitive key navigation for device operation, which is ergonomically desirable and advantageously reduces an amount of visual concentration needed to handle and operate the patient monitor. For example, in the displayed embodiment, the input keys are disposed along curve roughly parallel to the alignment edge 210. Additionally, the actual keys can provide increased navigation-by feel. In an embodiment, the keys include raised convex keys that feel like bumps on the surface of the housing. Such bumps may also comprise unique shapes or surface textures to further identify a respective input key and/or its function to the operator. For example, FIGS. 4A-4B show that during operation of the monitor 204, the alignment edge 210, the location and optionally the shape of the input keys of the keypad 208 advantageously provide the operator intuitive navigation-by-feel through the user input keys. Such navigation-by-feel enhances the single handed operation.

Figure 5:
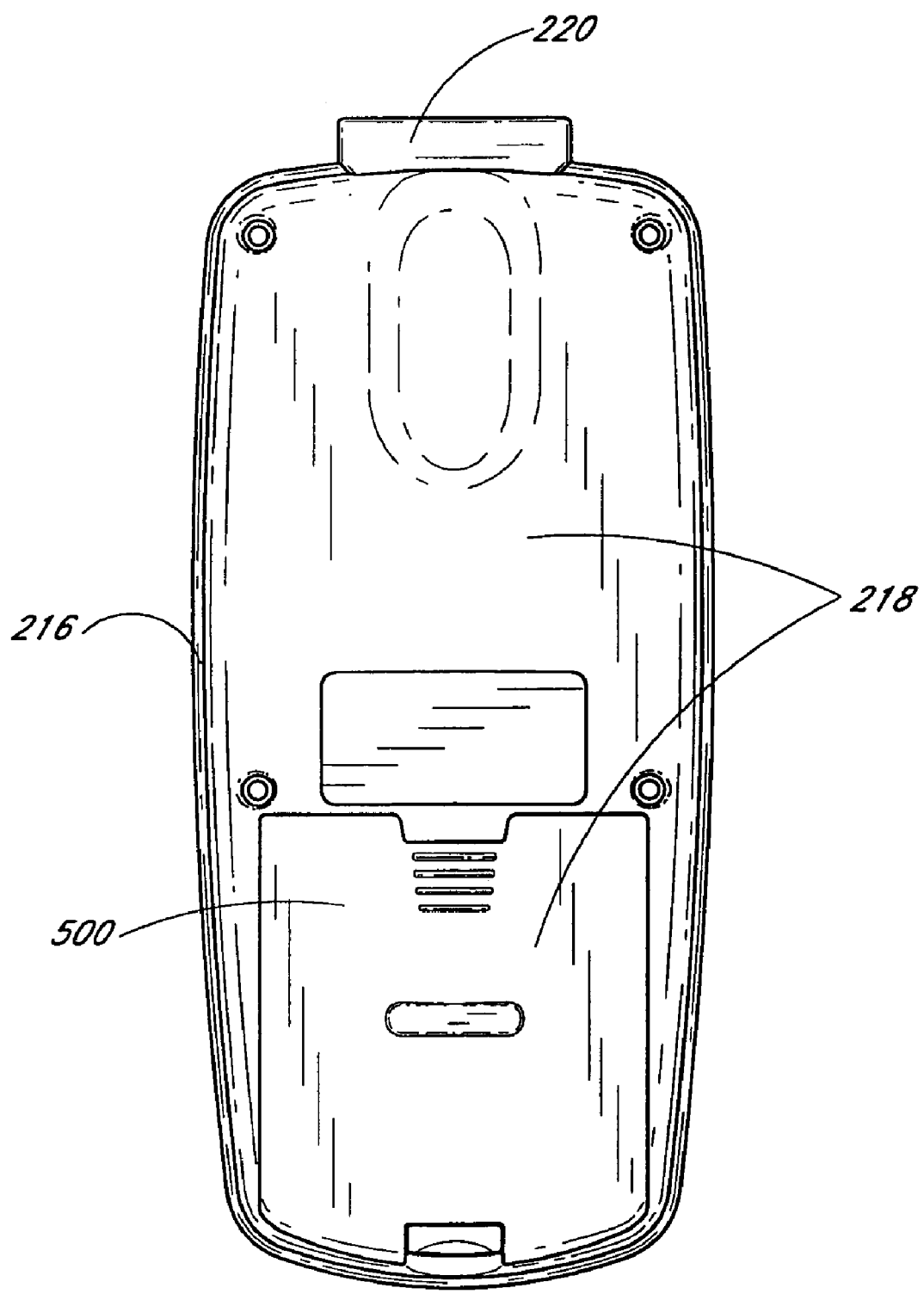
FIG. 5 illustrates a bottom plan view of an embodiment of the portable patient monitor of FIG. 2.
Figure 6:
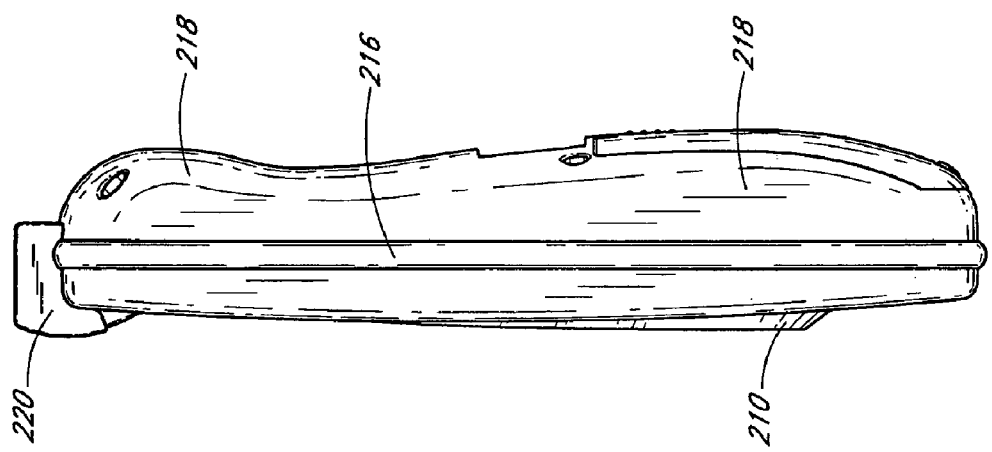
FIGS. 6-7 illustrate side elevation views of an embodiment of the portable pulse patient monitor of FIG. 2.
Figure 7:
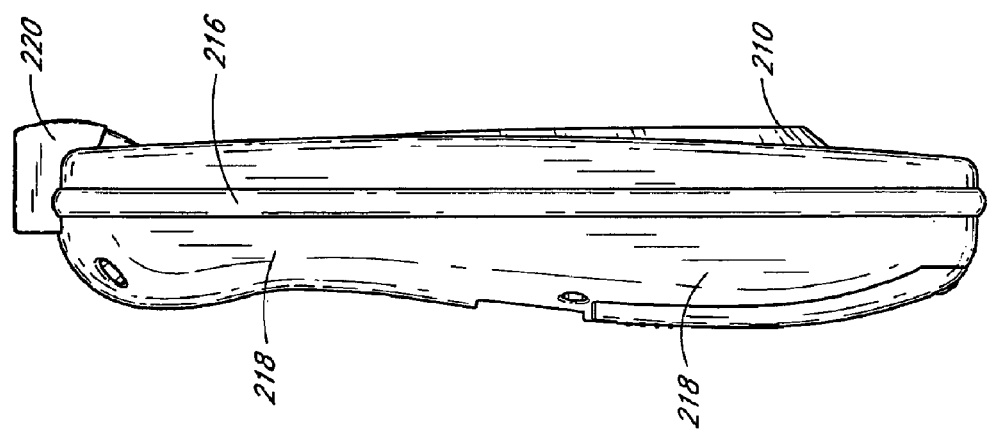
Figure 9:
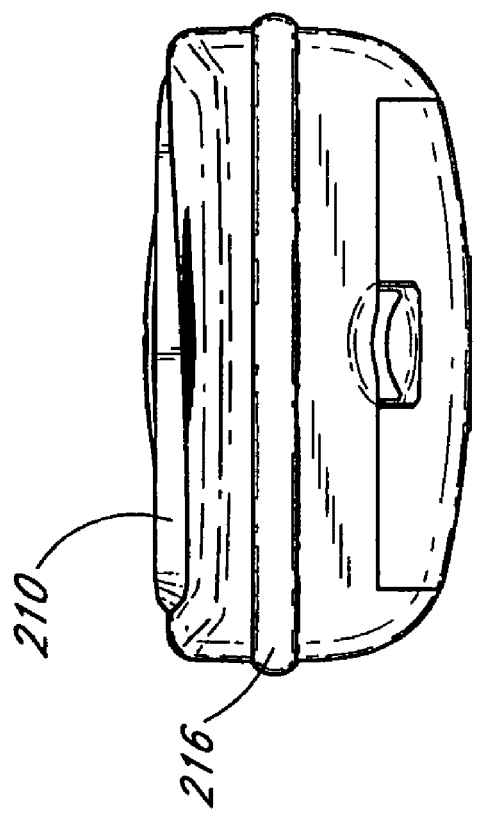
FIGS. 8-9 illustrate front and rear views of an embodiment of the portable patient monitor of FIG. 2.
Figure 8:
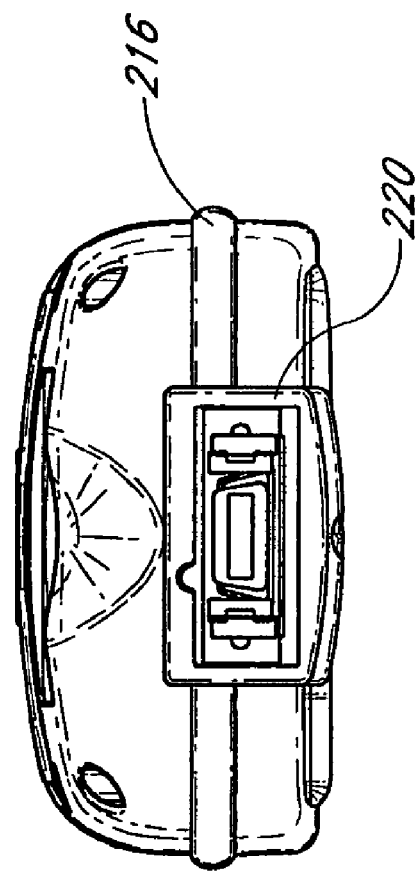

FIG. 5 illustrates a bottom view of the monitor 204 showing the bezel 216, the grip portions 218, and the cable connector 220. Moreover, FIG. 5 shows a battery compartment 500 usable to power the monitor 204. However, an artisan will recognize from the disclosure herein a wide variety of mechanisms for powering the monitor 204 including A/C adapters, power from other monitoring devices, automobile or other adapters, combinations of the same, or the like.

FIGS. 6-9 illustrate side, front, and rear views of the monitor 204 showing alternate views of the alignment edge 210, the bezel 216, the grip portions 218, and the cable connector 220.

Figure 10:
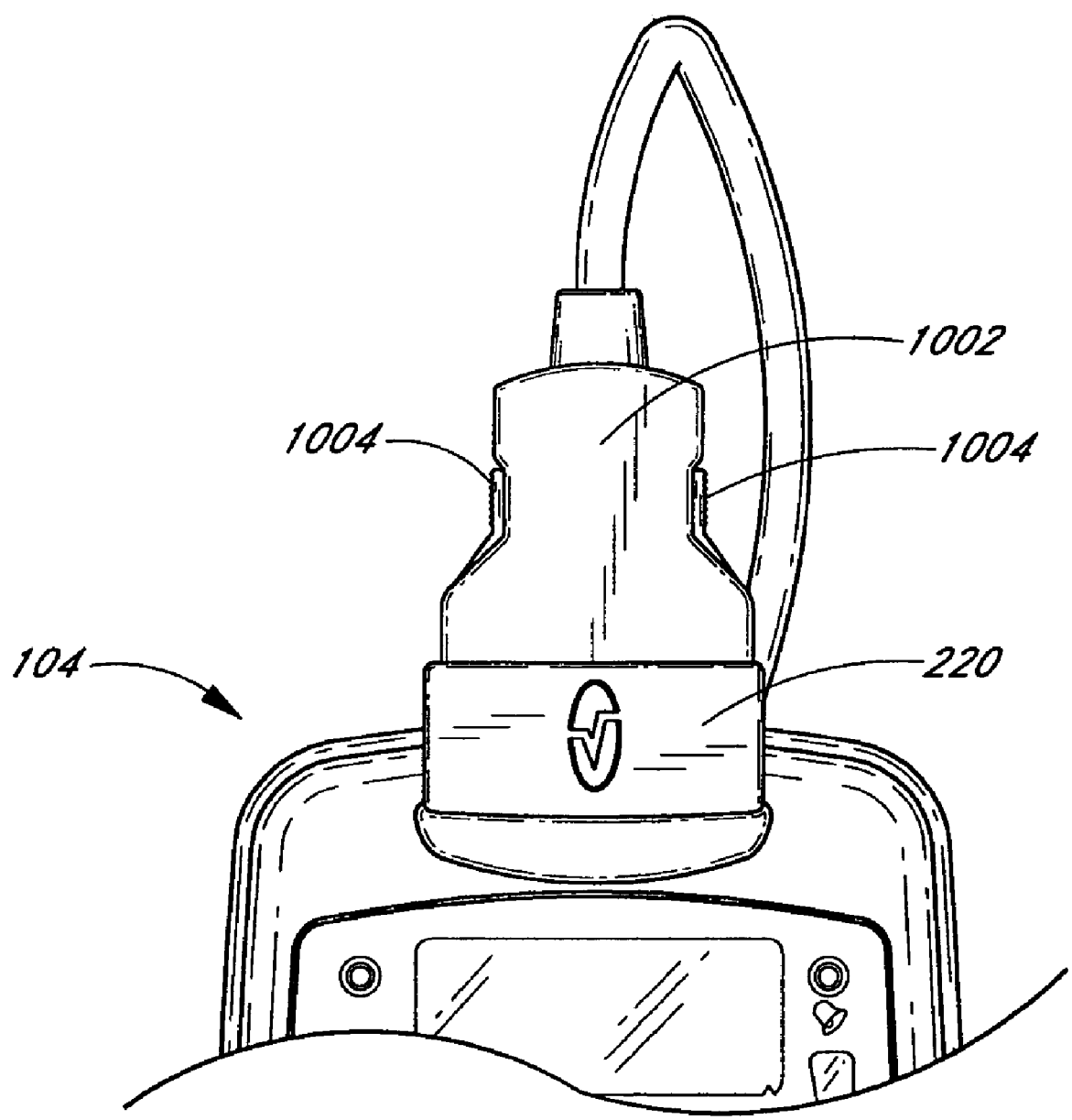
FIG. 10 illustrates a top plan view of a sensor cable connected to the portable patient monitor of FIG. 2.

FIG. 10 illustrates a top plan view of a sensor cable connector 1002 connected to the monitor 204. When connected, the sensor cable connector 1002 provides electronic communication between the cable connector 220 of the monitor 204, and one or more sensors, such as, for example, sensor 102. According to one embodiment, the sensor cable connector 1002 includes a locking mechanism releasable by activation of tabs 1004. The locking mechanism advantageously ensures against accidental electrical and/or mechanical separation of the connectors 220 and 1002. FIG. 10 also shows the cable connector 220 encompassing and shielding the electrical connection between the connectors 220 and 1002.

Figure 11A:
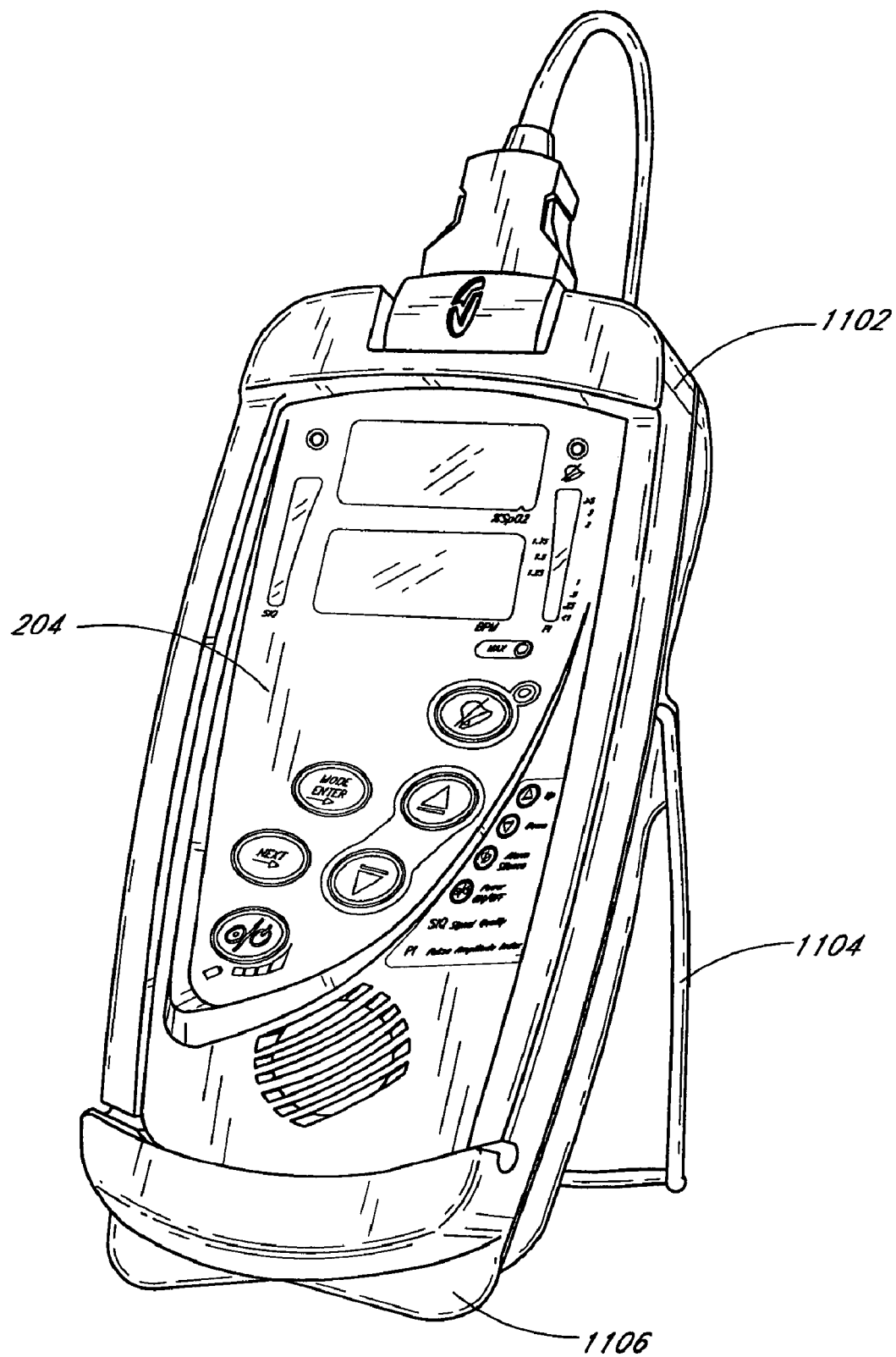
FIG. 11A illustrates a perspective view of an embodiment of a protective boot cover and stand for the portable patient monitor of FIG. 2.

FIGS. 11A-11B illustrate perspective views of an embodiment of a protective boot cover 1102 including a retractable table-top stand 1104. According to an embodiment, the protective boot cover 1102 is shaped to accept the monitor 204, without visually or mechanically blocking the display portion 206 or the keypad portion 208 of the top 203 of the monitor 204. As shown in FIGS. 11A-11B, the cover 1102 comprises a pliable material capable of absorbing at least a portion of the type of accidental impacts that may occur, such as, for example, from falling from a table or bed. The cover 1102 also comprises a stand, which in the illustrated embodiment, includes a swing arm 1104 and a balancing section 1106 which combine to allow an operator to place the monitor 204 in an angled position on a flat surface. The angled position advantageously allows the operator to read the monitor 204 from a horizontal point of view. In an embodiment, the swing arm 1104 can be rotated about its hinge to lie against and optionally within the cover 1102, thereby allowing the operator to also lay the monitor 204 flat on its backside while still within the cover 1102. Once the swing arm 1104 is in its closed and optionally locked position, the patient monitor 204 can advantageously be used as a portable monitor without removal from the protective boot 1102.

Figure 11C:
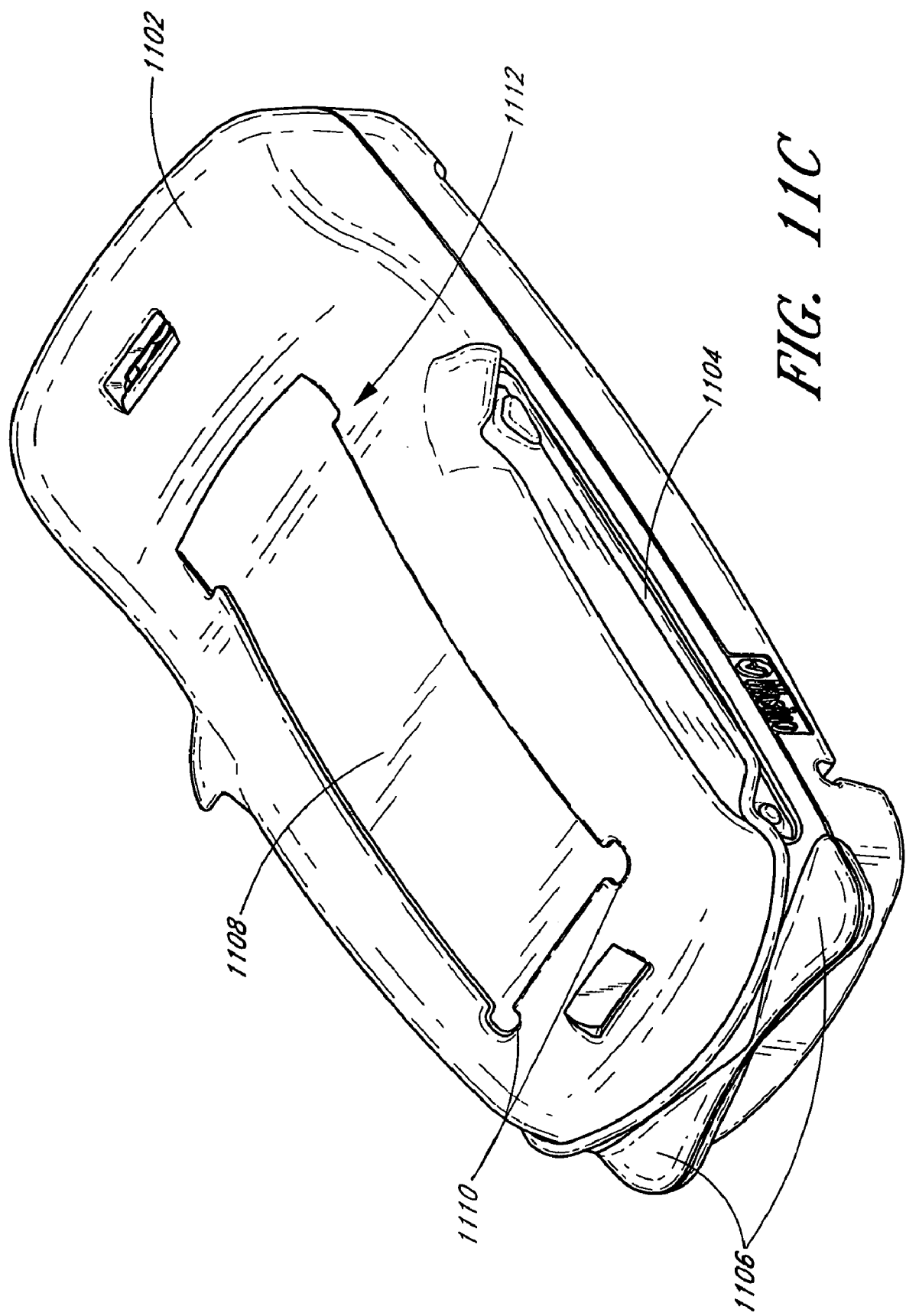

FIG. 11C illustrates a bottom perspective view of the protective boot cover 1102 including a retractable table-top stand 1104. As shown in FIG. 11C, the boot 1102 includes a documents clip 1108 including a fixed flexible end 1110 and an open end 1112. In an embodiment, a caregiver may slide documents such as medical records, trend data for one or more monitored physiological parameters, or the like, into the open end 1112 of the clip 1108. In an embodiment the slightly convex or curved shape of the clip 1108, along with the flexible fixed end 1110 advantageously exerts a small friction fit holding force on the documents such that documents placed within the boot 1102 will stay until removed. Thus, the clip 1108 advantageously allows caregivers a convenience area to store medical records associated with the monitored patient, the monitor 204, or the like.

While disclosed with reference to FIGS. 11A-11C, an artisan will recognize from the disclosure herein that the table-top stand 1104 can comprise a wide variety of mechanisms capable of standing the monitor 204 on its end. For example, the cover 1102 itself may form a stand, may be shaped to vitiate any balancing portions, may include electronic circuitry for charging or communicating with the monitor 204 (similar to a sync device for many handheld computers or cellular phones), or the like. Moreover, the documents clip may comprises a plurality of clips, a memory storage device holder, or other alternatively shaped clips recognizable to an artisan from the disclosure herein.

Figure 12A:
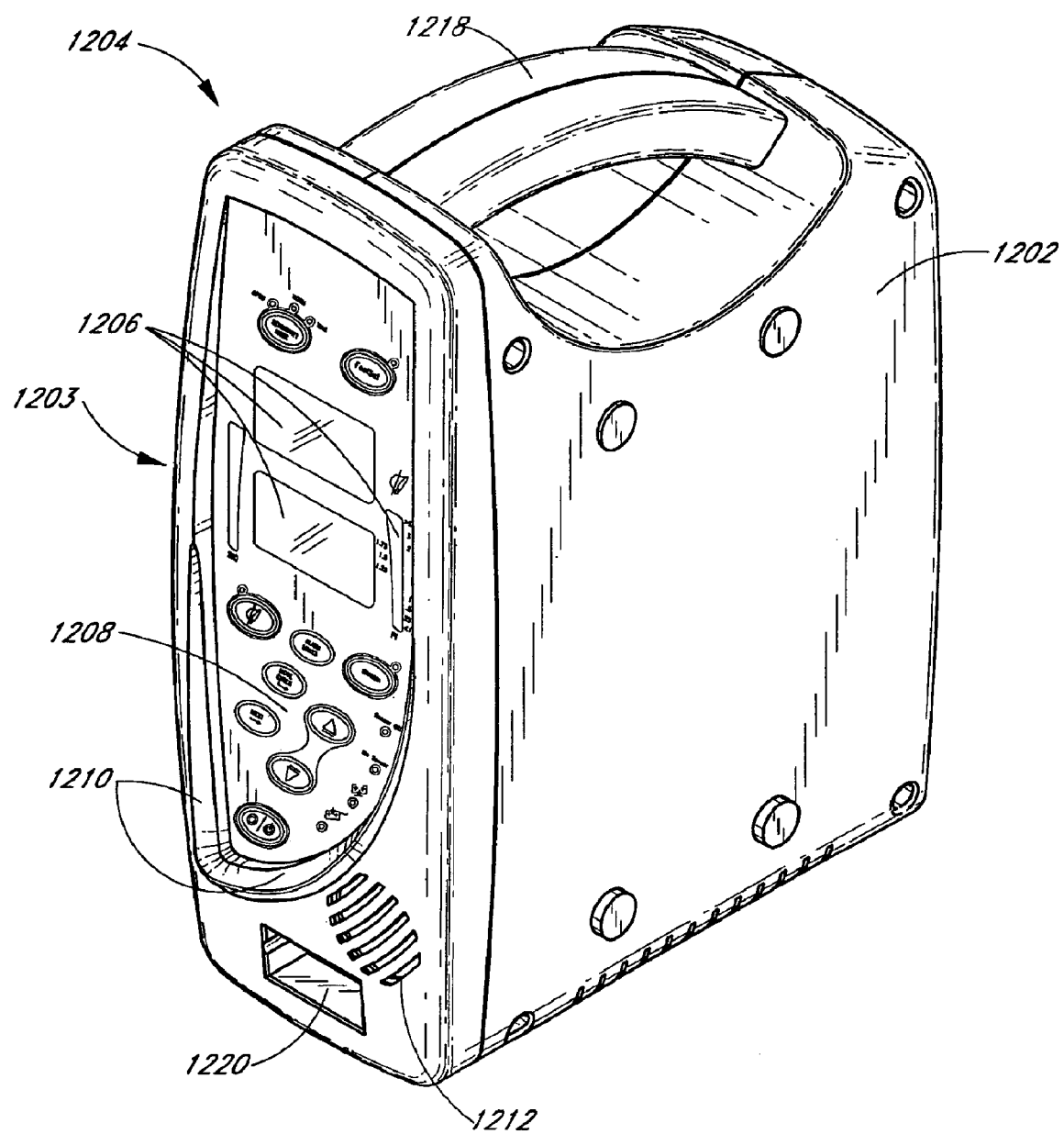
FIGS. 12A-12C illustrate vertical front perspective, horizontal front perspective and vertical rear perspective views of an embodiment of the portable patient monitor of FIG. 1, respectively.
Figure 12B:
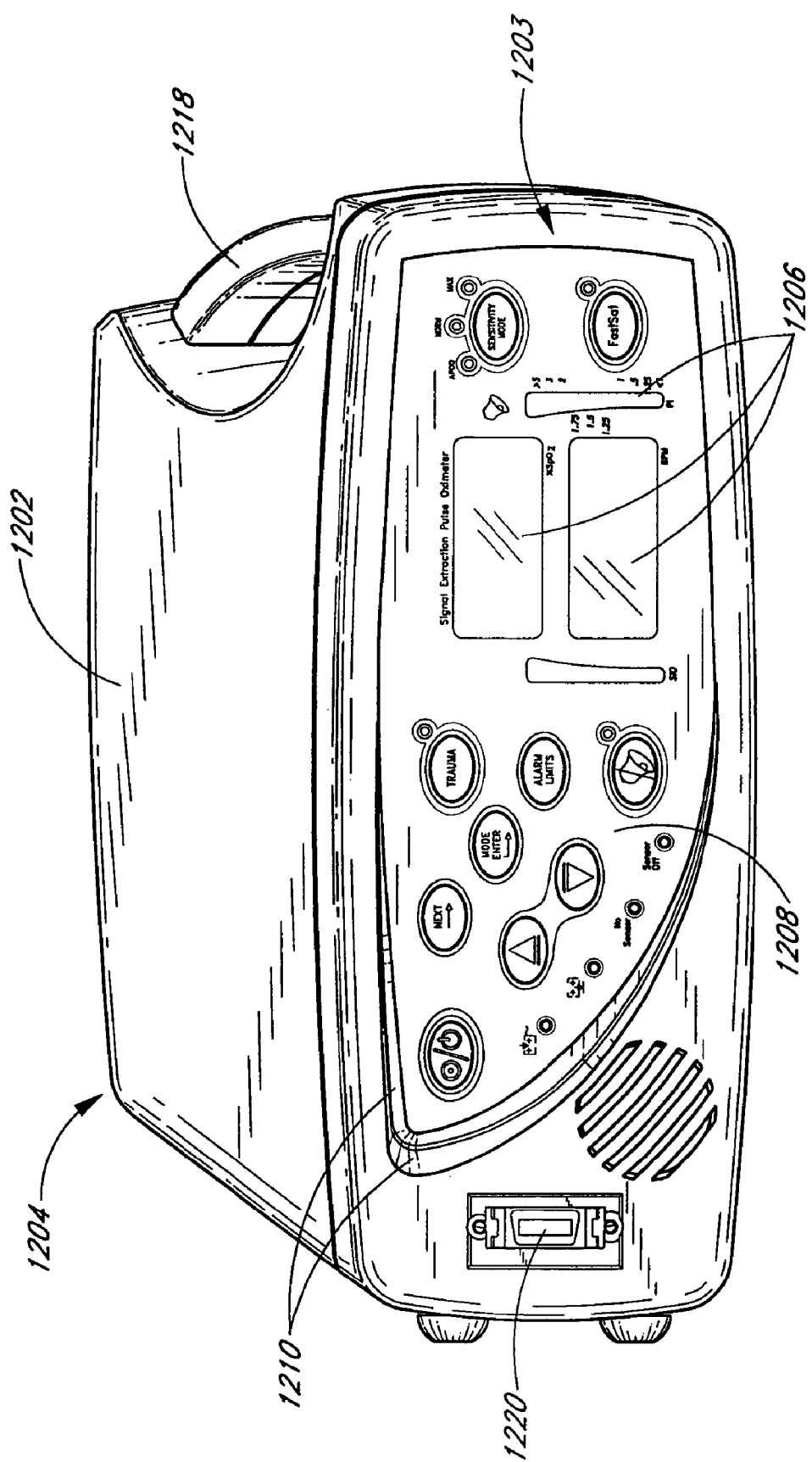

FIGS. 12A-18 illustrate views of another embodiment of a portable patient monitor 1204. According to one embodiment, the monitor 1204 comprises electronic circuitry comprising some or all of the circuitry capable of performing some or all of the functionality disclosed with reference to the monitors 104 and 204. As shown in FIG. 12A, the monitor 1204 includes a housing 1202 having a front side 1203 and a handle 1218. In an embodiment, the housing 1202 can rest on a substantially flat surface, such as a table or a bed, in a plurality of positions. For example, the housing 1202 can rest in a vertical position where the bottom side of the housing 1202 rests against the substantially flat surface (FIG. 12A), and in a horizontal position where the right side of the housing 1202 rests against the substantially flat surface (FIG. 12B). According to an embodiment, an orientation sensor may advantageously adjust the orientation of the display based on whether the monitor 1204 rests in the first or horizontal position. Discussion of oximeters capable of adjusting their orientation are commercially available from Masimo Corporation of Irvine California and are discussed in U.S. patent application Ser. No. 10/153,263, filed May 21, 2002, and its related patent and copending application family, which are incorporated herein by reference. In an embodiment, the portable patient monitor 1204 may be ordered as a vertical only monitor or as a horizontal only monitor depending upon the purchaser's desired orientation.

FIG. 12A also shows the handle 1218 comprising an arcuate section capable of allowing digits of a hand to comfortably slide around the handle 1218 to provide a sturdy and firm grip on the monitor 1204. The handle 1218 advantageously extends from a side of the monitor 1204 that provides easy access regardless of whether the monitor 1204 is lying in the vertical or horizontal position.

FIG. 12A also illustrates the monitor 1204 including an alignment edge 1210, a display portion 1206, a keypad 1208, a speaker grating 1212, and a cable connector 1220, all similar to those described with reference to monitors 104, 204.

Figure 12C:
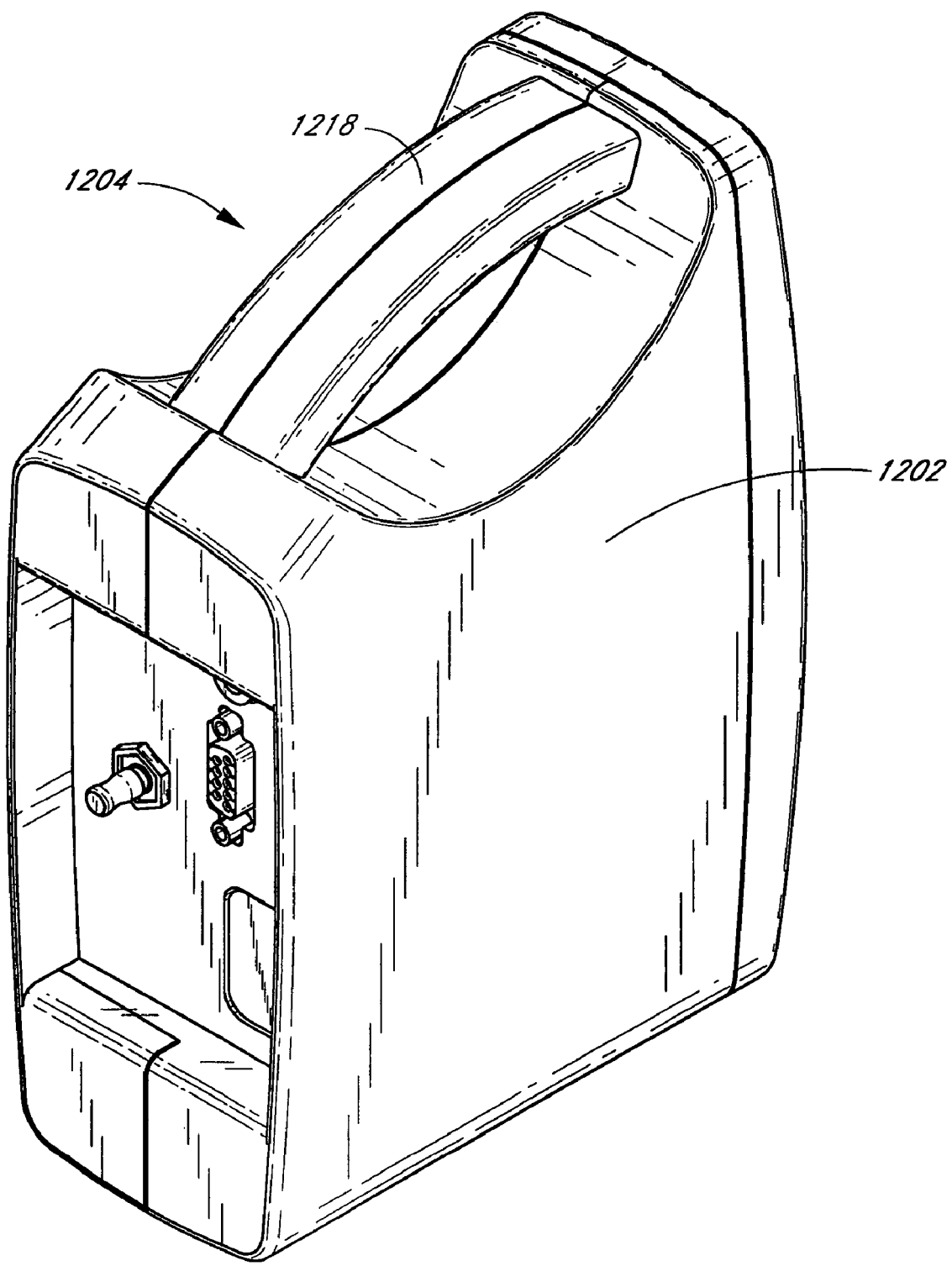

FIG. 12C illustrates a vertical rear perspective view of an embodiment of the portable patient monitor 1204. As shown in FIG. 12C, the monitor 1204 may include outputs for transferring data to, for example, legacy or other physiological parameter monitoring devices, computers, or the like. For example, the monitor 1204 may include an output conventionally associated with personal computing input/output devices, thereby advantageously allowing personal computing devices communication with the electronic circuitry, including the processor 116 of the monitor 1204. Such communication with personal computing devices may include data downloads for historical data, trend data, trace data, or the like for one or more monitored physiological parameters. The communication may also include data expected by the connected device, such as, for example, data appearing to the connected device to be originating with the sensor 102.

Figure 12D:
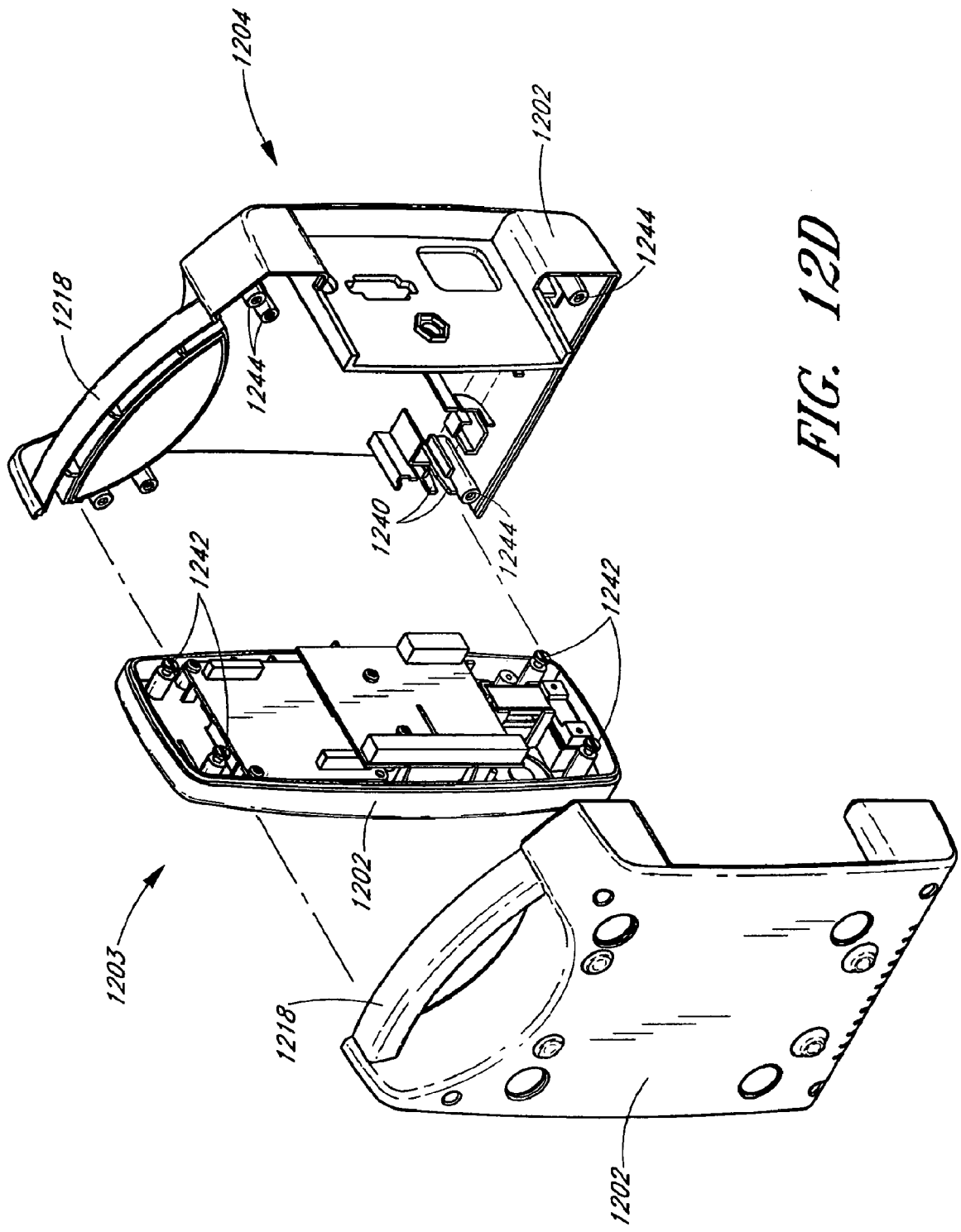
FIG. 12D illustrates an exploded vertical rear perspective view of an embodiment of the portable patient monitor of FIG. 12.
Figure 14:
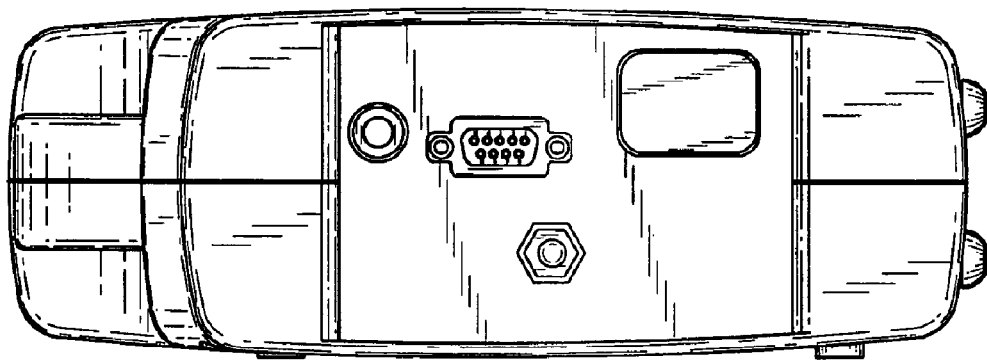
FIG. 14 illustrates a rear elevation view of an embodiment of the portable patient monitor of FIG. 12.

FIG. 12D illustrates an exploded vertical rear perspective view of an embodiment of the portable patient monitor 1204. As shown in FIG. 12D, the monitor housing 1202 may advantageously comprise a plurality of molded sections that allow for straightforward inclusion of electronic and other components during the manufacture of the monitor 1204. For example, FIG. 12D shows the monitor housing 1202 comprising three molded sections including two sides and a front section. The two side sections include a plurality of novel detents 1240 shaped substantially similar to the arms of a pair of scissors and adapted to capture exposed adjustment screws 1242 of the front section. Use of the detents 1240 and screws 1242 advantageously provide for adjustability in manufacture and rigidity after assembly. FIG. 12D also shows at least one side section including a plurality of cylindrical plastic extensions 1244 some or all of which are threaded to accept fasteners for pull the sides together and fixing the detents 1240 around the extended screws 1242. Although disclosed with reference to FIG. 12D, an artisan will recognize from the disclosure herein, various mechanical mateable structures usable for rigidly assembling the sections of the monitor 1204.

Figure 13:
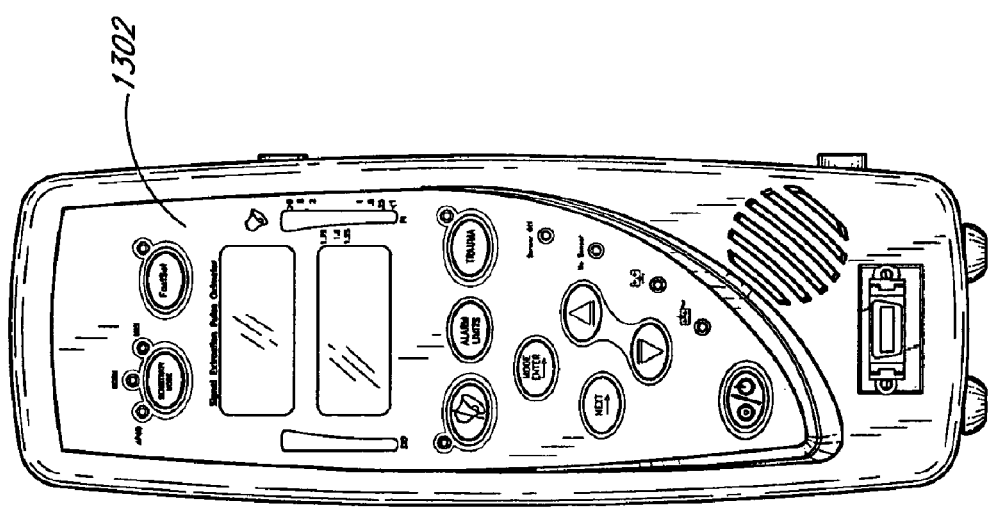
FIG. 13 illustrates a front elevation view of an embodiment of the portable patient monitor of FIG. 12.
Figure 16:
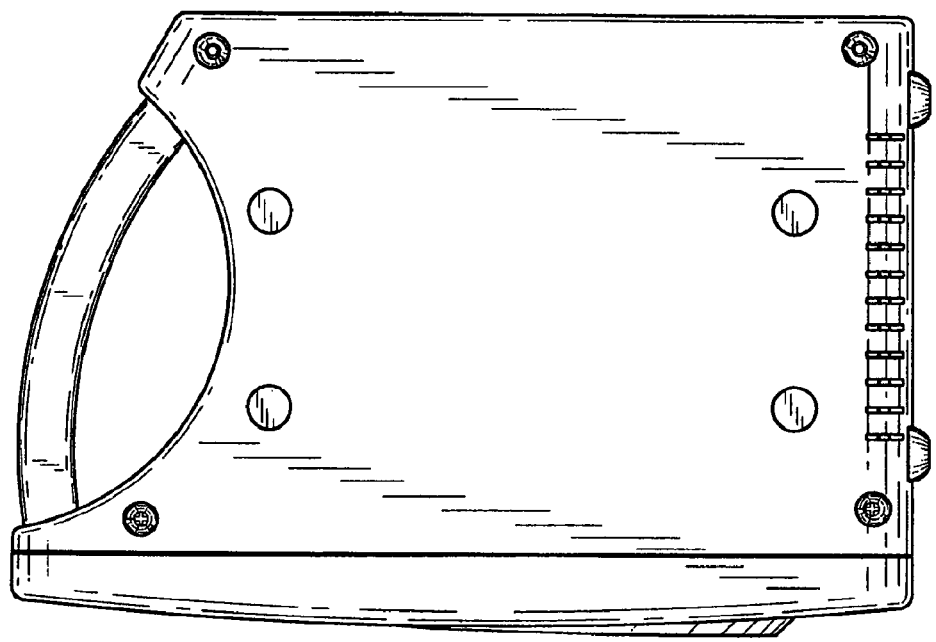
FIG. 16 illustrates a right side elevation view of an embodiment of the portable pulse patient monitor of FIG. 12.
Figure 15:
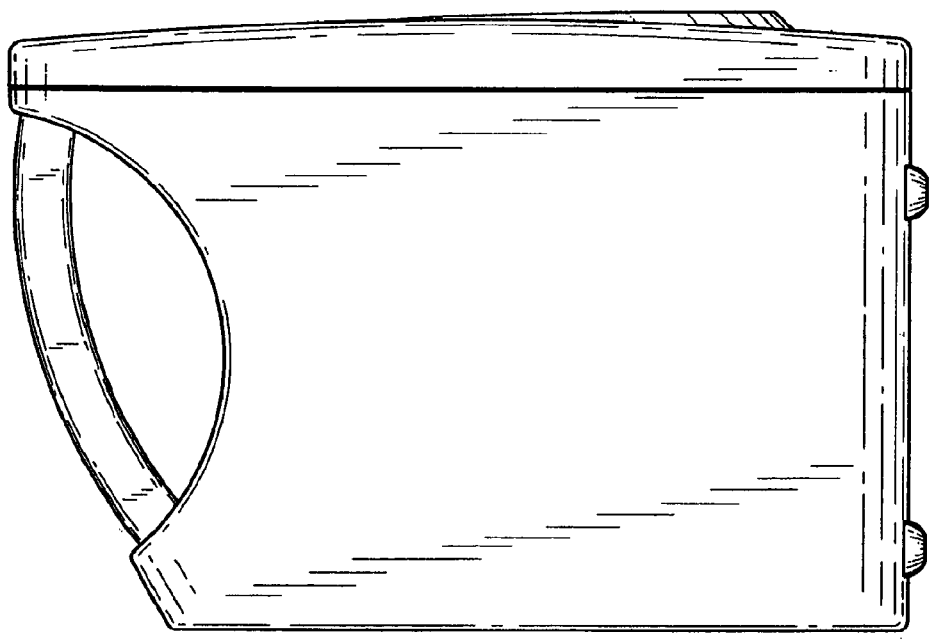
FIG. 15 illustrates a left side elevation view of an embodiment of the portable pulse patient monitor of FIG. 12.
Figure 18:
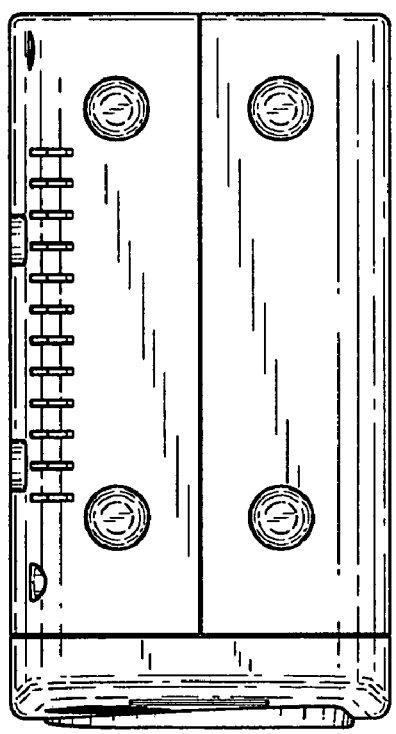
FIG. 18 illustrates a bottom plan view of an embodiment of the portable patient monitor of FIG. 12.
Figure 17:
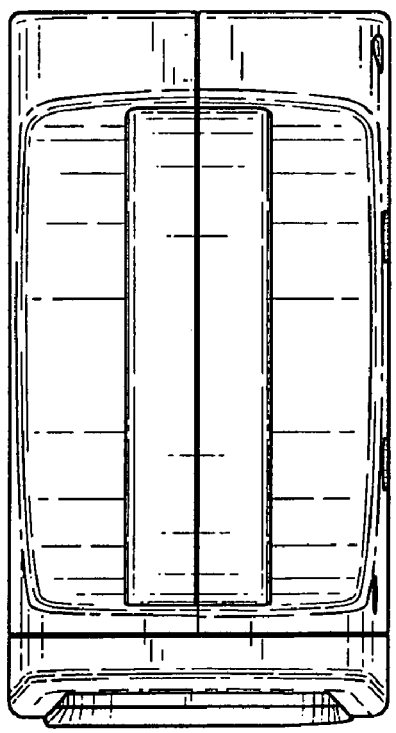
FIG. 17 illustrates a top plan view of an embodiment of the portable patient monitor of FIG. 12.

FIGS. 13-18 further illustrate various views of the portable patient monitor of FIG. 12. As shown in FIG. 13, the display panel 1302 advantageously comprises many of the display and user interface features disclosed with reference to monitors 104, 204, and 1204.

Figure 19:
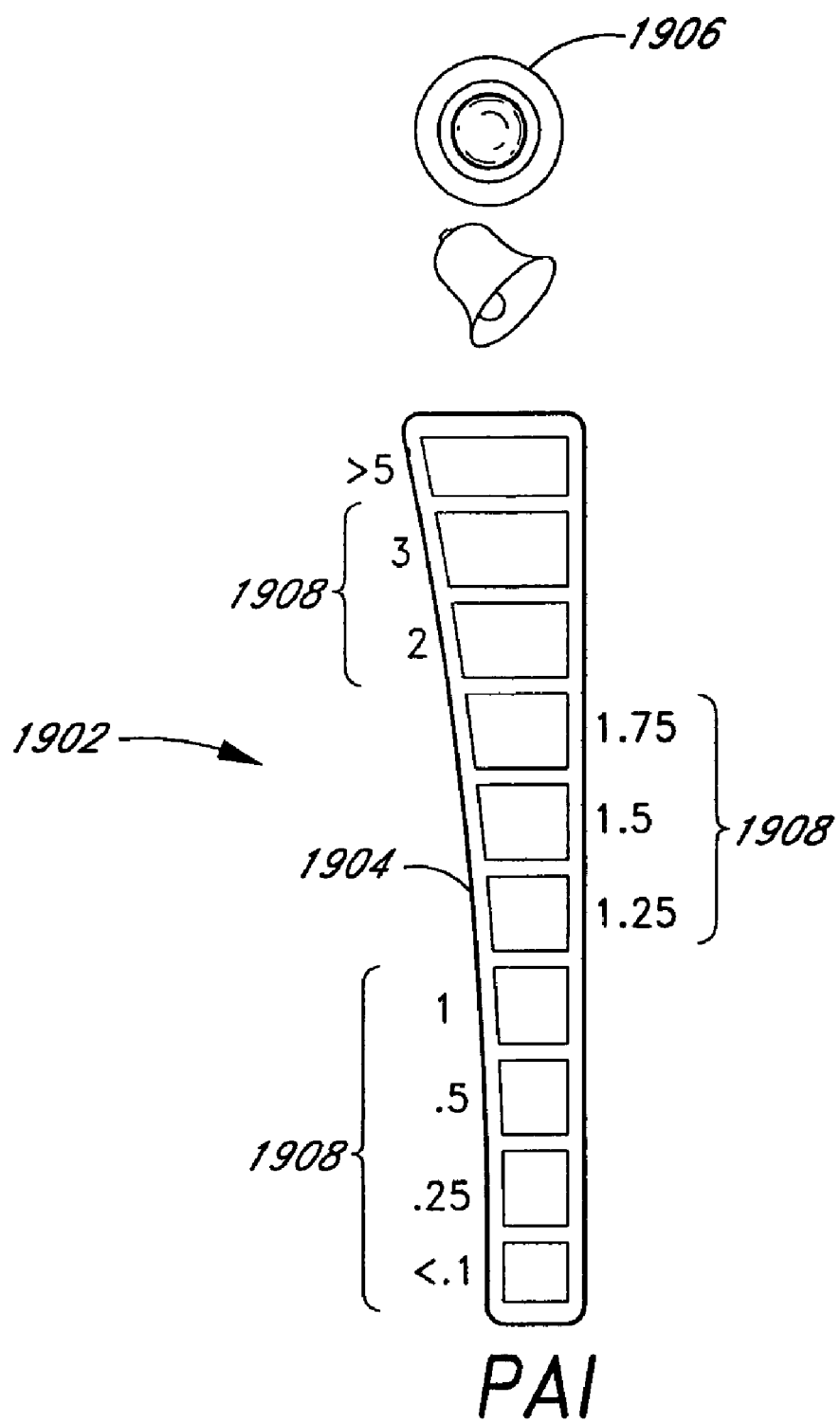
FIG. 19 illustrates an embodiment of a pulse amplitude index display of portable patient monitors such as those of FIG. 2 or FIG. 12.

FIG. 19 illustrates an embodiment of a pulse amplitude index (PAI) display 1902 in the form of an LED bar graph 1904 and single LED visual alarm 1906. The PAI can be used as a diagnostic tool during low perfusion for the accurate prediction of illness severity, especially in neonates. Moreover, the rate of change in the PAI can be indicative of blood loss, sleep arousal, sever hypertension, pain management, the presence or absence of drugs, or the like According to one embodiment, the PAI values may comprises a measurement of the signal strength of the arterial pulse as a percentage of the total signal received. For example, in one preferred embodiment, the alternating portion of at least one intensity signal from the sensor 102 may advantageously be divided by the static portion of the signal. For example, an infrared intensity signal may advantageously be used for the PAI determination as it is less subjective to noise.

In an embodiment, a PAI of below about 1.25% may indicate medical situations in need of caregiver attention, specifically in monitored neonates. Because of the relevance of about 1.25%, the monitors 104, 204, and 1204 may advantageously include level indicia 1908 where the indicia 1908 swap sides of the graph 1904, thus highlighting any readings below about that threshold. Moreover, behavior of the graph 1904, as discussed above, may advantageously draw attention to monitored values below such a threshold.

As discussed above, the monitors 104, 204, and 1204 may include output functionality that outputs, for example, trend perfusion data, such that a caregiver can monitor the PAI over time. Alternatively or additionally, one or more of the monitors 104, 204, and 1204 may display historical trace data on an appropriate display indicating the monitored PAI values over time.

In one embodiment, the graph 1904 shows a static value of perfusion for a given time period, such as, for example, one or more pulses. In other embodiment or functional setting, the graph 1904 may advantageously pulse with a pulse rate, may hold the last reading and optionally fade until the next reading, may indicate historical readings through colors or fades, or the like. In a preferred embodiment, the LED bar 1908 is highest and green when the perfusion at the measurement site is best, and lowest and red when the perfusion is worst. Moreover, LED 1906 may advantageously light, or optionally flash, when the perfusion falls below a predetermined threshold, or may show the current status, such as, for example, good perfusion—green, cautionary perfusion—yellow, and/or poor perfusion—red. Moreover, an artisan will recognize from the disclosure herein a wide variety of straightforward to complex alarm rules attempting to reduce the number of false alarms caused by the calculated perfusion values dropping below a threshold. Additionally, the audible indicator 124 of the monitors 104, 204, and 1204 may sound in conjunction with and/or addition to the LED 1906.

Figure 20C:
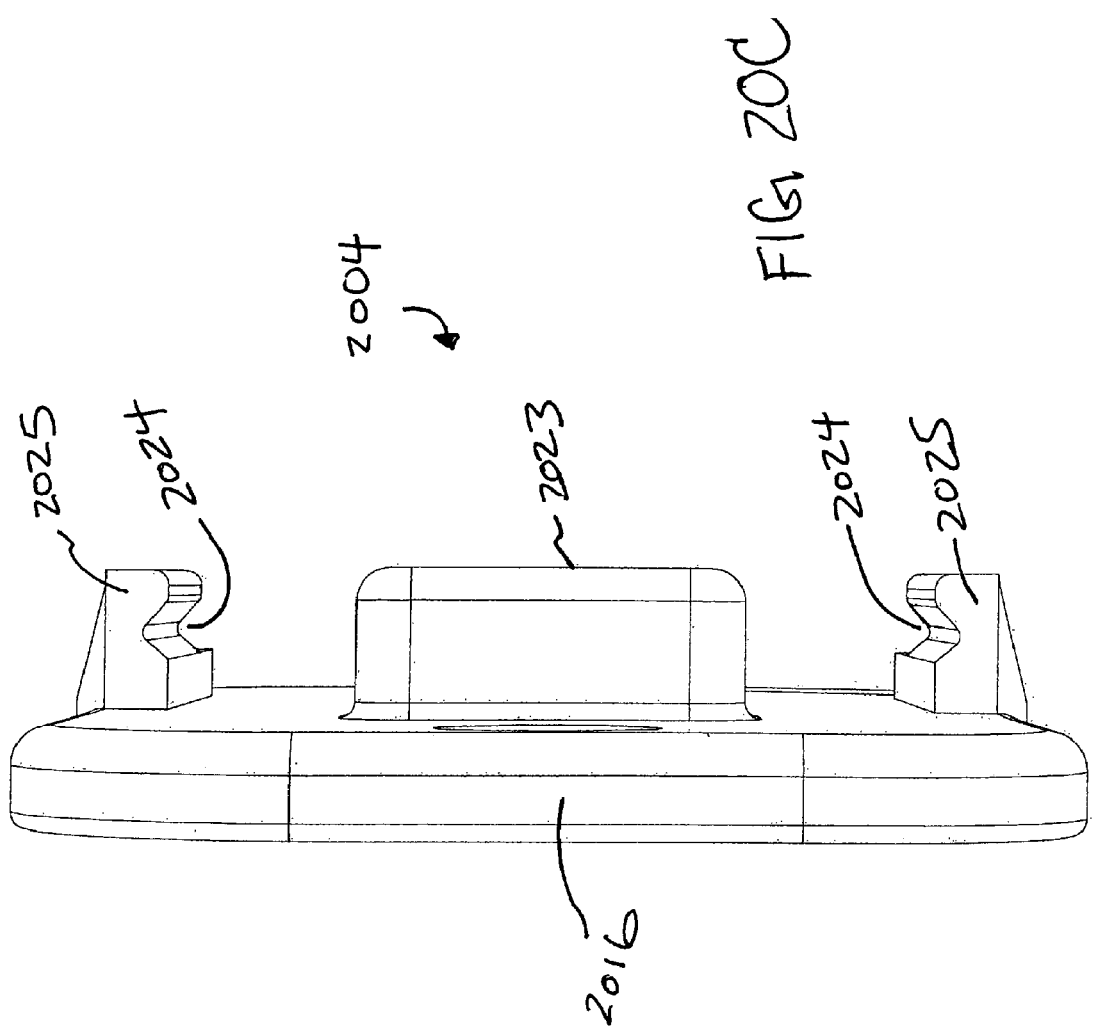

FIGS. 20A-20D illustrate perspective views of exemplary releasably matable mechanical latching mechanisms 2002, 2004 for attaching a portable patient monitor to another surface, such as a device, a wall, a bed, or the like. As shown in FIG. 20A, a male latching mechanism 2002 includes a body 2006 having attachment mechanisms 2008 for affixing the body 2006 to one of a monitor or other surface. In an embodiment, the male latch 2002 includes a releasing tongue 2010 having a wedge-shaped catch 2012. In an embodiment, the tongue 2010 is hingably attached to the body 2006 and is biased in a closed position using, for example, structural memory. The catch 2012 is positioned on the tongue 2010 in a manner to decrease an amount of force applied to the tongue 2010 that will release the catch 2012 from a locked position. The body 2006 also includes a stop 2013. In addition, the male latch 2002 includes outwardly protruding edges 2014 of rails 2015 raised from the body 2006. In an embodiment, the rails 2015 are wedge-shaped down at least a portion of their long axes.

FIG. 20B and 20C show an exemplary female latching mechanism 2004 including a body 2016 having attachment mechanisms 2018 for affixing the body 2016 to one of a surface or a monitor. In an embodiment, the body 2016 includes a wedge-shaped catch 2022, a stop 2023, and grooves 2024 in rails 2025 raised from the body 2016.

Figure 20D:
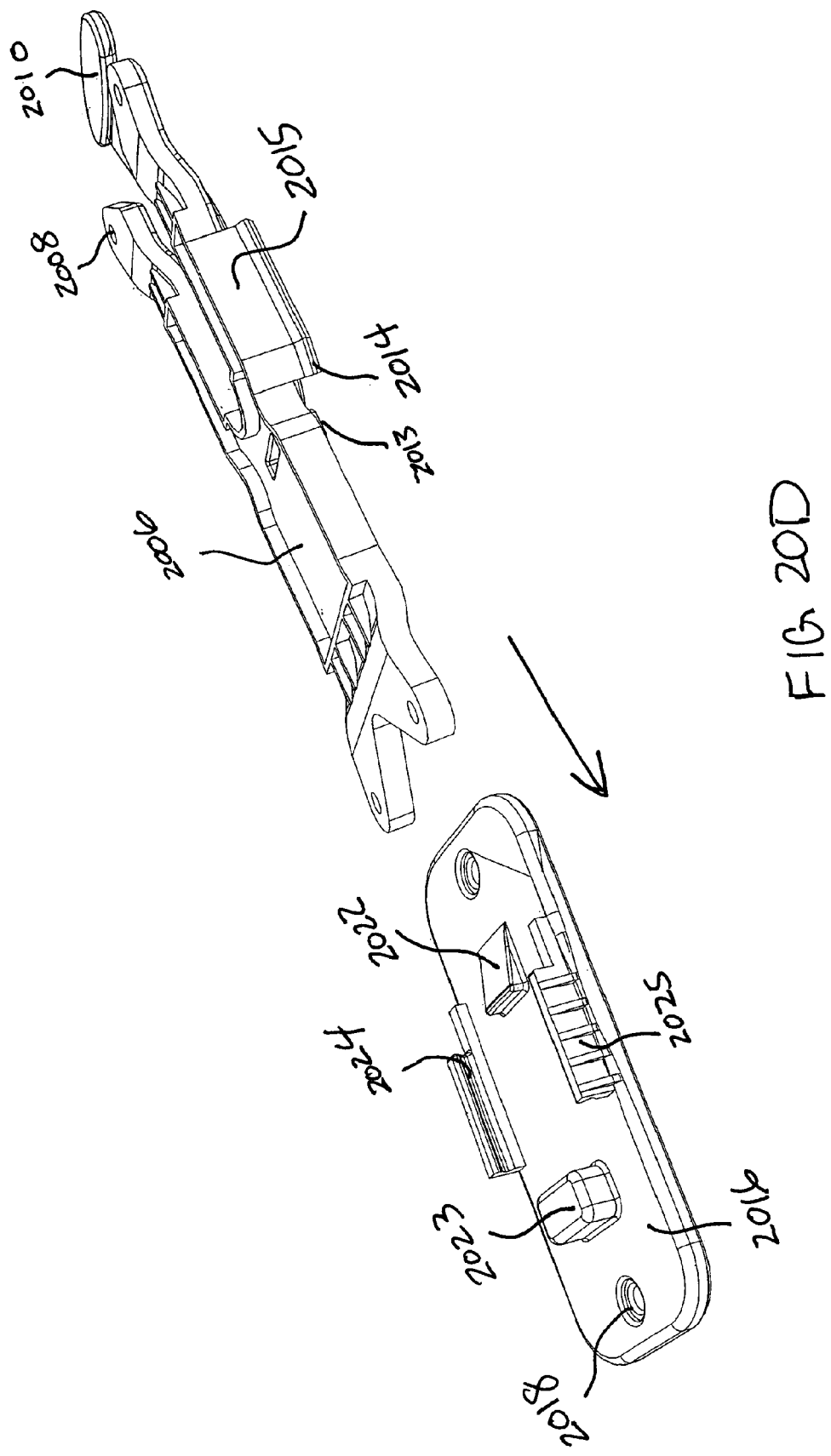

FIG. 20D shows the male and female latch portions 2002, 2004 positioned such that the outwardly protruding edges 2014 of the rails 2015 of the male latch 2002 slide within the grooves 2024 of the rails 2025 of the female latch 2004 until the tongue 2010 hinges inwardly as the catch 2012 passes over the opposing catch 2022, then snaps back outwardly as the stop 2013 abuts the stop 2023 and locks the monitor to the surface. Once in the locked position, at least the protruding edges 2014 and the grooves 2024, as well as the stop 2013 and stop 2023 assist in tightly securing a monitor to another surface, such as, for example, another monitoring device. Release of the latches 2002, 2004, is accomplished by depressing the tongue 2010 until the tongue 2010 hinges inwardly sufficiently to pass the catch 2012 over the opposing catch 2022 and allow the male latch 2002 to slide out.

Although defined with respect to a specific male and female latching portions, an artisan will recognize from the disclosure herein a wide variety of latching mechanism for attaching one or more of the monitors 104, 204, and 1204 to other instruments, surfaces, walls, beds, or the like.

Additionally, other combinations, omissions, substitutions and modifications will be apparent to the skilled artisan in view of the disclosure herein. Accordingly, the present disclosure is not intended to be limited by the reaction of the preferred embodiments, but is to be defined by reference to the appended claims. Moreover, all publications, patents, and patent applications mentioned in this specification are herein incorporated by reference to the same extent as if each individual publication, patent, or patent application was specifically and individually indicated to be incorporated by reference.

What is claimed is:

1. A portable patient monitoring device including navigation by feel functionality, the device comprising:
    electronic circuitry capable of receiving a signal output from a light sensitive detector capable of detecting light attenuated by body tissue carrying pulsing blood, wherein the electronic circuitry is also capable of outputting audio or visual indicia indicative of one or more physiological parameters of the body tissue;
    a housing including a top side;
    a plurality of user input keys arranged on the top side of the housing along the periphery of at least two substantially parallel curves;
    a protective cover comprising a pliable material;
    at least one alignment edge substantially parallel to the two curves, a portion of said at least one alignment edge being raised substantially above a substantially planar surface of said top side of said housing, said edge locatable by feel of the user to guide the user to the plurality of user input keys.

2. The portable patient monitoring device of claim 1, wherein the housing comprises a handheld housing.

3. The portable patient monitoring device of claim 1, wherein the two curves are substantially diagonal to the housing and wherein each diagonal includes more than one user key.

4. The portable patient monitoring device of claim 1, wherein the two curves are irregular.

5. The portable patient monitoring device of claim 1, wherein the two curves roughly corresponds to a sweeping motion of a user's thumb across the top side of the housing on a hand in which the user holds the portable patient monitoring device.

6. The portable patient monitoring device of claim 1, wherein the two curves each includes a radius roughly corresponding to a user's thumb on a hand in which the user holds the portable patient monitoring device.

7. The portable patient monitoring device of claim 6, wherein each of the two curves roughly corresponds to the radius.

8. The portable patient monitoring device of claim 1, wherein one or more of the user input keys are shaped to allow a user to differentiate by feel between the top side of the housing and the one or more of the user input keys.

9. The portable patient monitoring device of claim 8, wherein the user input keys comprise a raised convex shape.

10. The portable patient monitoring device of claim 1, wherein the at least one alignment edge partially surrounds the user input keys.

11. The portable patient monitoring device of claim 10, wherein the at least one alignment edge forms a rough "V" shape.

12. The portable patient monitoring device of claim 1, wherein the housing includes surfaces other than said alignment edge shaped to position a user's index fingers around the housing to form a secure grip.

13. The portable patient monitoring device of claim 1, wherein the protective cover comprises a pliable impact resistive housing surrounding at least a portion of the housing of the portable patient monitoring device.

14. The portable patient monitoring device of claim 1, further comprising a table-top stand.

15. The portable patient monitoring device of claim 1, wherein the visual indicia comprises at least blood oxygen saturation data.

16. The portable patient monitoring device of claim 1, wherein the visual indicia comprises a pulse amplitude indication data.

17. The portable patient monitoring device of claim 1, wherein the visual indicia comprises a pulse rate.

18. The portable patient monitoring device of claim 1, wherein the visual indicia comprises a measurement of perfusion through the body tissue.

19. The portable patient monitoring device of claim 1, further comprising an impact resistant bezel surrounding a periphery of said housing.

20. A patient monitor comprising:
    a handheld housing including a generally planer top surface, said housing having a periphery at least partially comprising a pliant material capable of reducing an effect of an impact against said housing;
    a plurality of displays arranged on the generally planer surface in a generally flush manner with said surface, at least two of said plurality of displays are configured to display visual indicia different from one another yet both responsive to physiological parameters of a patient being monitored;
    a plurality of user keys raised above said generally planer surface, said user keys being locatable-by-feel by a holder of the patient monitor;
    a guide surface raised above said generally planer surface in an area proximate said user keys, said guide surface substantially flush with said generally planer surface in an area proximate said displays such that said guide surface rises from a flush position to a raised position between said area proximate said displays to said area proximate said user keys in a substantially uniform manner along a length thereof, said guide surface providing a locate-by-feel mechanism for a user seeking the user keys with the user's fingers.

* * * * *